United States Patent [19]
McEvily et al.

[11] Patent Number: 5,059,438
[45] Date of Patent: Oct. 22, 1991

[54] COMPOSITIONS AND METHODS FOR INHIBITING BROWNING IN FOODS USING RESORCINOL DERIVATIVES

[75] Inventors: Arthur J. McEvily, Weston; Radha Iyengar, Belmont; Akiva Gross, Newtown, all of Mass.

[73] Assignee: Enzytech, Inc., Cambridge, Mass.

[21] Appl. No.: 537,361

[22] Filed: Jun. 13, 1990

Related U.S. Application Data

[63] Continuation-in-part of Ser. No. 475,150, Feb. 5, 1990, abandoned.

[51] Int. Cl.$^5$ .................................................. A23B 7/00
[52] U.S. Cl. ...................................... 426/268; 426/270; 426/380; 426/331; 426/541; 564/170
[58] Field of Search ............... 426/310, 599, 615, 268, 426/269, 321, 323, 326, 333, 263, 327, 332, 376, 643, 654, 658, 541; 564/170

[56] References Cited

U.S. PATENT DOCUMENTS

| | | |
|---|---|---|
| 3,305,366 | 2/1967 | Sutton et al. |
| 3,337,348 | 8/1967 | White et al. |
| 3,754,938 | 8/1973 | Ponting |
| 3,859,450 | 1/1975 | Alsina |
| 3,982,030 | 9/1976 | Alsina |
| 4,814,192 | 3/1989 | Sapers et al. |
| 4,818,549 | 4/1989 | Steiner et al. |
| 4,900,564 | 2/1990 | Lee et al. |
| 4,981,708 | 1/1991 | McEvily ............................ 426/262 |

FOREIGN PATENT DOCUMENTS

| | | |
|---|---|---|
| 0275710 | 7/1988 | European Pat. Off. |
| 0341664 | 11/1989 | European Pat. Off. |
| WO89/11227 | 11/1989 | World Int. Prop. O. |

OTHER PUBLICATIONS

J. D. McCord and A. Kilara, *J. of Food Science*, 48:1479–1483 (1983).
J. Zawistowski et al., *Can. Inst. Food Sci. Tech.*, 20:162–165 (1987).
J. R. L. Walker, *Food Technology*; 11:341–345 (1976).
M. B. Faulkner et al., *Advanced Food Research*, 19:302–310 (1953).
T. P. Labuza, *Cereal Foods World*, 34(4):353 (1989).
D. D. Duxbury (Ed.), *Food Processing*. Apr., 1990, p. 44.
T. Labuza, *Seafood Leader*, May/Jun. (1990).
S. H. Kelly and B. J. Finkle, *J. Sci. Fd. Agric.*, 20:629–632 (1969).
J. R. L. Walker and E. L. Wilson, *J. Sci. Fed. Agric.*, 26:1925–1831 (1975).
P. G. Pifferi et al., *J. Sci. Fd. Agric.*, 25:263–270 (1974).
G. M. Sapers et al., *J. Food Science*, 54(4):997–1012 (1989).
M. W. Montgomery, *J. Food Science*, 48:951–952 (1983).
O. J. Ferrer et al., *J. Food Science*, 54(2):478–480 (1989).
R. Singh and T. R. Ahlawat, *J. Food Sci. Tech.*, 10:172–175 (1973).
Enzyme Development Corporation Technical Bulletin, "Prevention of Melanosis in Shrimp with Enzeco ® Ficin".
Enzyme Development Corporation Technical Bulletin, "Treatment of Prawns with Enzeco ® Ficin to Prevent Melanosis".
Ponting et al., *J. Food Science*, 37:434–436 (1972).
J. K. Palmer and J. B. Roberts, *Science*, 157:200–201 (1967).
C. T. Shannon and D. E. Pratt, *J. Food Science*, 32:479–483 (1967).
W. S. Otwell and M. Marshall, *In: Proceedings of the Eleventh Annual Tropical and Subtropical Fisheries Conference of the Americas*, pp. 35–44.
H. Heymann et al., *J. Am. Soc.*, 76:6330–6335 (1954).
G. Schneider and S. Schmidt, *Z. Physiol. Chem.*, 315:20–27 (1959).
D. A. Robb et al., *Phytochemistry*, 5:665–675 (1966).
D. Richter, *Biochem. J.*, 76:901–908 (1934).

*Primary Examiner*—Carolyn Paden
*Attorney, Agent, or Firm*—Hamilton, Brook, Smith & Reynolds

[57] ABSTRACT

Resorcinol derivatives are disclosed as inhibitors of enzymatic browning in foods and beverages such as shrimp, apples, fruit juices and wines.

43 Claims, 13 Drawing Sheets

COMPOSITIONS AND METHODS FOR INHIBITING BROWNING IN FOODS USING RESORCINOL DERIVATIVES

RELATED APPLICATIONS

This application is a continuation-in-part of U.S. patent application Ser. No. 07/475,150 filed Feb. 5, 1990, now abandoned, by A. J. McEvily, R. Iyengar and A. Gross, the entire disclosure of which is hereby incorporated herein by reference.

BACKGROUND

Browning of foods is a major problem in the food and beverage industry. Browning, or oxidative darkening, can be the result of the action of an enzyme, such as polyphenol oxidase (PPO), or the result of non-enzymatic chemical reactions, for example, due to polymerization of phenolic compounds which are present in some foods. High PPO activity is present in foods which are susceptible to browning, e.g., shrimp, bananas and mushrooms. Browning causes deleterious changes in the appearance and texture of foods and beverages. Both enzymatic and non-enzymatic browning constitute serious problems for the food industry and result in millions of pounds of wasted food products per year.

Enzymatic browning, in particular, has been the subject of much research, particularly as the causative agent of shrimp melanosis, which is characterized by the formation of dark spots on shrimp. Faulkner et al., *Advanced Food Research*, 19:302–310 (1953). Enzymatic browning is the result of PPO-catalyzed oxidation of mono- and diphenols to o-quinones which polymerize spontaneously to form dark-colored, high molecular weight polymers, leading to the characteristic browning or formation of dark spots.

Several methods have been developed to prevent browning, including heat inactivation of PPO and various chemical treatments, such as altering the pH of the food. Heat inactivation is not appropriate for fresh foods, such as fruits and seafood, as the high temperatures necessary to inactivate PPO change the quality and texture of the foods. Likewise, reducing the pH by adding an acid (e.g., citric acid or phosphoric acid) deleteriously affects the appearance and quality of some foods.

The control of PPO-catalyzed enzymatic browning in mushrooms using citric acid was reported by McCord and Kilara in the *Journal of Food Science*, 48:1479–1483 (1983). The inhibition of polyphenol oxidase activity in an extract of Jerusalem artichokes using various sulfite compounds was described in Zawistowski et al., in *Can. Inst. Food Sci. Tech. J.*, 20(3):162–164 (1987). The use of cinnamic acid, p-coumaric acid and ferulic acid to control enzymatic browning in fruit juices was described by J. R. L. Walker in *Food Technology*, 11:341–345 (1976). T. C. Wong et al. report in *Plant. Physiol.*, 48:24–30 (1971) that phloroglucinol and resorcinol, and their derivatives d-catechin and orcinol react with 4-methyl-o-quinone which is formed by PPO in peaches, although these compounds are not substrates for PPO. R. Kuttner and H. Wagreich, *Arch. Biochem. Biophys.*, 43:80–87 (1952) report that mushroom PPO (catecholase) is inhibited by benzoic acid and selected benzoic acid derivatives. None of these methods have proven entirely satisfactory, however, due to expense, lack of availability, or inferior performance.

Labuza in *Cereal Foods World*, 34(4):353 (1989) describes the use of proteases especially ficin, in the control of enzymatic browning of certain foods. The author attributed this effect to attack on PPO by the protease.

Another method for reducing browning which has been prevalent in the food industry is adding sulfite salts to foods and beverages. Some forms of enzymatic browning, such as shrimp melanosis, have traditionally been treated by dipping or coating the shrimp or other food in a sulfite solution, such as sodium bisulfite. Sulfites are also added to wines to prevent oxidation. Sulfites reduce o-quinones to the mono- and/or diphenols thereby inhibiting the browning reaction. However, the use of sulfite in foods has been restricted due to adverse health effects in certain individuals, and may be restricted further or even eliminated completely.

SUMMARY OF THE INVENTION

The invention relates to compounds and methods for inhibiting oxidative browning of foods and beverages, particularly enzymatic browning caused by PPO activity. The compounds are resorcinol derivatives having the general formula:

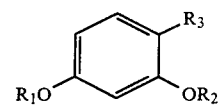

Formula I wherein $R_1$ and $R_2$ are independently selected from the group consisting of: H, $CH_3$, $COR'$, $CR'$, $PO_3R'R''$ and $SO_3R'R''$ wherein $R'$ and $R''$ are independently H or an alkyl group having from 1 to about 6 carbon atoms in a linear, branched or cyclic configuration or a substituted aromatic compound; and $R_3$ is an organic or inorganic substituent selected so that the resulting compound has inhibitory activity. For example, $R_3$ can be a heteroatom or a group containing a heteroatom, a saturated or unsaturated alkyl group, a substituted aromatic compound or an organic functional group selected so that the compound has inhibitory activity. The heteroatom can include, for example, oxygen (O), nitrogen (N), sulfur (S), phosphorus (P) or halogens such as chlorine (Cl) bromine (Br), iodine (I) or fluorine (F). The saturated or unsaturated alkyl group can have from 1 to 30 carbon atoms in a linear, branched or cyclic configuration and can include a substituted aromatic compound. The alkyl substitutents or organic functional groups can contain a heteroatom or heteroatoms, for example oxygen (O), nitrogen (N), sulfur (S), phosphorus (P) or halogens such as chlorine (Cl), bromine (Br), iodine (I) or fluorine (F). 4-Alkyl resorcinol compounds are particularly effective for inhibiting melanosis in most foods. For example, 4-hexylresorcinol, (wherein $R_1$ and $R_2$ are both H and $R_3$ is $C_6H_{13}$) which has the following formula:

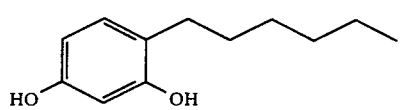

Formula II is highly effective for this purpose.

In one embodiment, $R_3$ has the general structure:

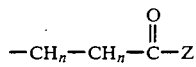

wherein n is 1 or 2 and Z is an alkyl or other organic functional group selected so that the compound has inhibitory activity. Z can be an alkyl substituent containing at least one heteroatom such nitrogen (N), oxygen (O), sulfur (S) or phosphorus (P) or halogens such as chlorine (Cl), bromine (Br), iodine (I) or fluorine (F). In a preferred embodiment, Z is selected from the group consisting of: OH, $NH_2$, $O(CH_2)_xCH_3$, $NHCO_2(CH_2)_xCH_3$, $NH(CH_2)_xCH_3$, amino acids, polyamine metabolites, such as $NH(CH_2)_xNH_2$; $NH(CH_2)_xNH(CH_2)_yNH_2$; $NH(CH_2)_xNHR_4$; and $NH(CH_2)_xNH(CH_2)_yNHR_4$ wherein x and y independently can be any integer from 0 to 5; and higher polyamine oligomers or substituted oligomers consisting of at least three monomers, wherein the monomer is a 1,ω diaminoalkane and $R_4$ has the following formula:

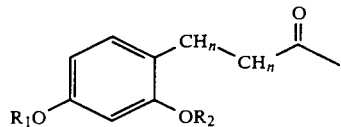

wherein n, $R_1$ and $R_2$ are as defined above. Compounds which are particularly effective inhibitors of oxidative browning are resorcinol derivatives having the general formula:

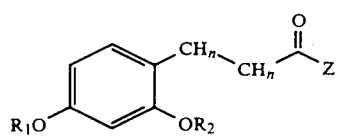

Formula III wherein n is 1 or 2 and $R_1$ and $R_2$ and Z are as defined above.

Particularly useful resorcinol derivatives for inhibiting enzymatic browning are obtained when n=2, $R_1$ and $R_2$ are both H and Z is OH, $NH(CH_2)_4NH_2$, $NH(CH_2)_4NHR_4$ (i.e., where x=4 and $R_4$ is as defined above,) or $NH(CH_2)_4 NH(CH_2)_3NHR_4$ (where x=4, y=3 and $R_4$ is as defined above). These compounds are shown as Formulae IV, V, VI and VII respectively:

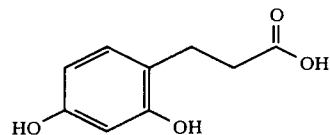

Formula IV

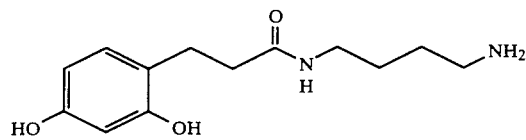

Formula V

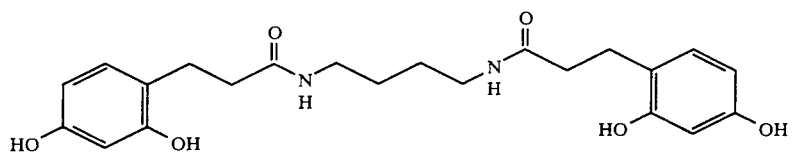

Formula VI

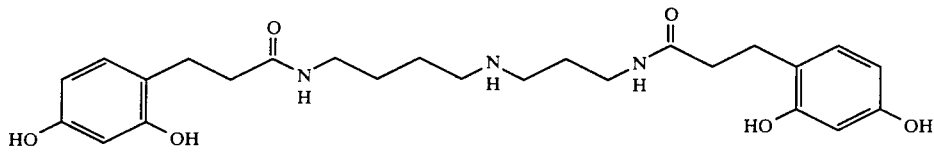

Formula VII

The substituted resorcinols represented by general Formula I comprise a class of compounds which are highly effective in inhibiting the browning of foods. 4-Hexylresorcinol, which is a commercially available compound, is particularly effective for this purpose. Of the derivatives represented by Formula III, three of these compounds were isolated from a natural source and their structures unambiguously determined by standard analytical organic chemistry procedures. specifically $^1$H and $^{13}$C NMR and mass spectra. These three specific derivatives have the structures represented by Formulae IV, V and VII, respectively Formula V, VI and VII represent polyamine derivatives which have not previously been isolated and/or characterized, whereas Formula IV represents a resorcinol derivative which had not previously been found in nature.

Methods of preparing anti-browning compositions containing resorcinol derivatives are also the subject of the present invention. Certain resorcinol derivatives can be prepared synthetically or isolated from natural sources such as plants. In one embodiment, the derivatives are isolated and purified to homogeneity from a botanical source, e.g., fig latex, by the steps of aqueous extraction, ultrafiltration, ion exchange chromatography and reverse phase HPLC.

A method of inhibiting browning of foods using the present compounds is described. In this method, foods which are susceptible to browning, including, for example, certain shellfish, crustaceans, fruits, vegetables and beverages, such as fruit juices and wines are treated with a composition containing an amount of the present resorcinol derivatives sufficient to inhibit the browning reaction.

The present resorcinol derivatives represented generally by Formulae I and III, and specifically by Formulae II and IV, and the resorcinol-polyamine derivatives represented specifically by Formulae V, VI and VII, are very effective in inhibiting browning in foods. The present compositions and methods are more effective than crude latex preparations and sodium bisulfite in inhibiting oxidative browning. Smaller amounts of the present compositions are needed to inhibit browning in most foods than the amounts of sodium bisulfite which are presently used to obtain the same level of inhibition. The present compounds provide an effective treatment for inhibiting or preventing browning in selected foods and beverages, without adversely affecting the appearance, taste, texture or quality of the food or beverage.

DETAILED DESCRIPTION OF THE INVENTION

Figure 1:
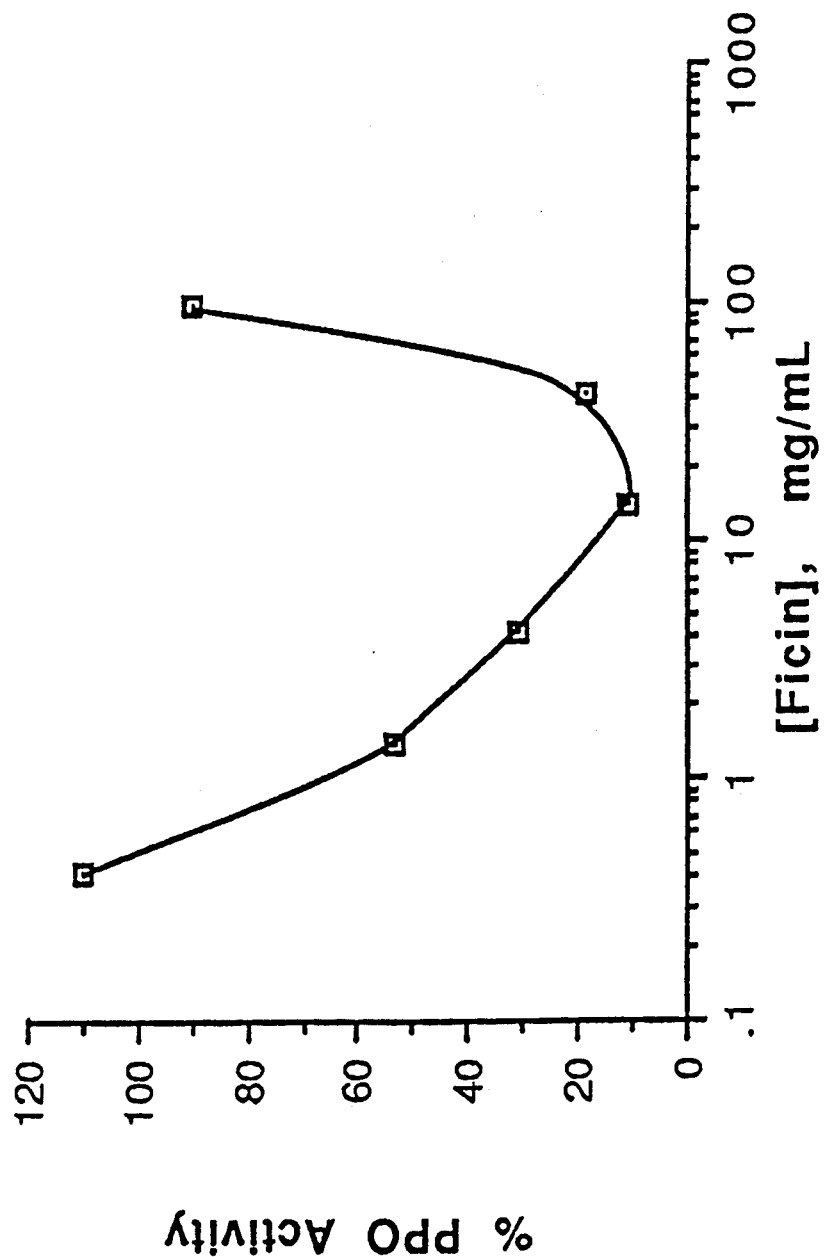
FIG. 1 is a graph comparing the effects of sodium bisulfite and various concentrations of a YM5 extract (F100) on the formation of melanosis in shrimp.

The present invention is based on the discovery that a class of resorcinol derivatives, some of which occur naturally in plants, can inhibit browning of foods. The present compounds are resorcinol derivatives which have the general formula shown as Formula I:

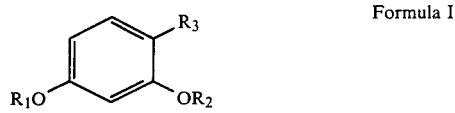

Formula I wherein $R_1$ and $R_2$ are independently selected from the group consisting of: H, $CH_3$, COR', CR', $PO_3R'R''$ and $SO_3R'R''$ wherein R' and R'' are independently H or an alkyl group having from about 1 to about 6 carbon atoms in a linear, branched or cyclic configuration or a substituted aromatic compound; $R_3$ can be a heteroatom or a group containing a heteroatom or a saturated or unsaturated alkyl group, a substituted aromatic compound or an organic functional group selected so that the compound has inhibitory activity. The heteroatom can include, for example, oxygen (O), nitrogen (N), sulfur (S), phosphorus (P), halogen such as chlorine (Cl), bromine (Br), or fluorine (F). The saturated or unsaturated alkyl group can have from 1 to 30 carbon atoms in a linear branched, or cyclic configuration or a substituted aromatic compound. The alkyl substitutents or organic functional group can contain a heteroatom or heteroatoms, for example oxygen (O), nitrogen (N), sulfur (S), phosphorus (P) or a halogen such as chlorine (Cl), bromine (Br), iodine (I) or fluorine (F).

Alkyl resorcinol compounds are particularly effective for inhibiting melanosis in most foods. For example 4-hexylresorcinol, which has the following formula:

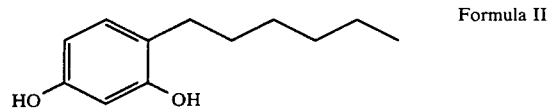

Formula II is very effective for this purpose.

In one embodiment $R_3$ has the general structure:

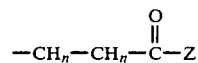

wherein n is 1 or 2, and Z is an alkyl or organic functional group selected so that the compound has inhibitory activity. Z can be an alkyl substituent containing at least one heteroatom, for example, nitrogen (N), oxygen (O), sulfur (S) and phosphorus (P) or a halogen such as chlorine (Cl), bromine (Br), iodine (I) or fluorine (F). In a preferred embodiment, Z is selected from the group consisting of: OH, $NH_2$, $O(CH_2)_xCH_3$, $NHCO_2(CH_2)_xCH_3$, $NH(CH_2)_xCH_3$, amino acids (such as lysine, ornithine, serine or cysteine); a polyamine metabolite such as $NH(CH_2)_xNH_2$, $NH(CH_2)_xNH(CH_2)_yNH_2$, $NH(CH_2)_x$ $NHR_4$ and $NH(CH_2)_xNH(CH_2)_yNHR_4$ wherein x and y can be an integer from 0 to 5; and polyamine oligomers or substituted polyamine oligomers consisting of at least three monomers, wherein the monomer is a 1,ω diaminoalkane and $R_4$ has the following formula:

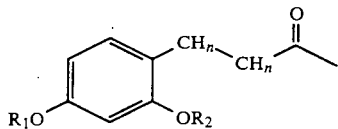

wherein n, $R_1$ and $R_2$ are as defined above.

Compounds which are also very effective inhibitors of oxidative browning are resorcinol derivatives having the following general formula:

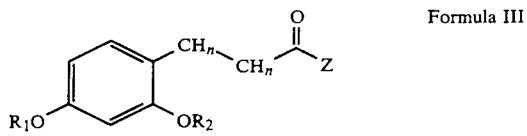

Formula III wherein n is 1 or 2 and $R_1$, $R_2$ and Z are as defined above.

Particularly useful resorcinol derivatives for inhibiting enzymatic browning are obtained when $n=2$, $R_1$ and $R_2$ are H and Z is OH, $NH(CH_2)_4NH_2$, $NH(CH_2)_4NHR_4(x=4$ and $R_4$ is as defined above) or $NH(CH_2)_4NH(CH_2)_3NHR_4(x=4$, $y=3$, and $R_4$ is as defined above). These compounds have the formulae shown as Formulae IV, V, VI and VII respectively:

C. M., and Signs, M. W. (1989) in *Plant Nitrogen Metabolism. In: Recent Advances in Phytochemistry*, Vol. 23, (E. E. Conn, Ed.) Plenum Press, New York. The hydroxycinnamic amide (HCA) derivatives of diaminobutane: p-coumaryldiaminobutane, ferulyldiaminobutane, caffeoyldiaminobutane, and di-p-coumaryldiaminobutane; and of spermidine: p-coumarylspermidine, have been found in 13 families of higher plants (Martin-Tanguy, J. (1985) *Plant Growth Regul.* 3, 381–400) and are believed to be involved in flower development. The HCAs are closely related in structure to Formulae V, VI and VII. Although much research is currently being performed on HCAs, there are no prior accounts in the literature on the presence of Formulae V, VI and VII. Formulae V and VII are novel, naturally-occurring polyamine derivatives. The compound of Formula VI, which has not been found in nature at this time, also represents a previously unknown polyamine derivative. Besides their efficacy as inhibitors of PPO-catalyzed melanosis, the compounds represented by Formulae V, VI and VII represent a novel class of polyamine derivatives whose distribution, metabolism and physiological effects are unknown.

The molecules shown as Formulae IV, V and VII can be purified from plants. Preparations from various botanical sources are effective inhibitors of certain enzymatic reactions. For example, latex derived from the fig tree, Ficus sp. (F.sp.) contains a protease, ficin. P. T.

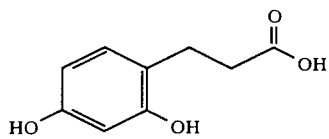

Formula IV

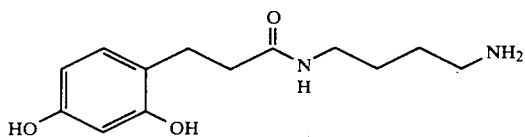

Formula V

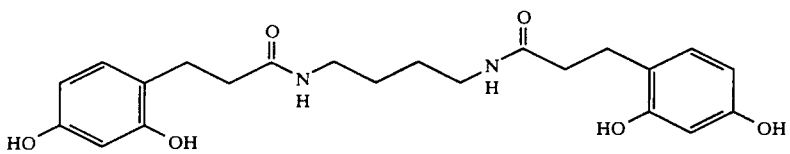

Formula VI

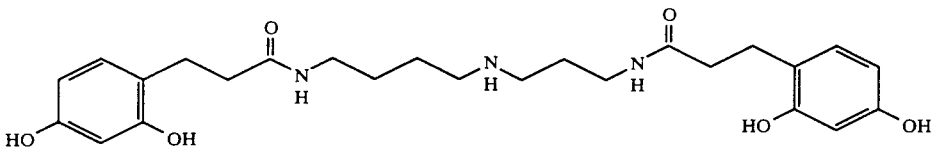

Formula VII

The invention includes functional equivalents of these formulae (Formulae I-VII). The term "functional equivalents" means a chemical derivative or analog of the compound which has similar anti-browning activity. As used herein, a molecule is said to be a "derivative" of another molecule when it contains additional or different chemical moieties not normally part of the molecule.

Analyses of the structures of Formulae V, VI and VII show the resorcinol moieties linked through an amide bond to diaminobutane (V and VI) and spermidine (III), respectively. The diamine diaminobutane, and the polyamine spermidine, are amino-acid derived aliphatic nitrogeneous compounds widely distributed throughout the plant and animal kingdoms. Flores, H. E., Protacio, Englund et al., *Biochemistry*, 7:163 (1963). Extracts containing ficin prepared from the fig latex have been shown to be effective inhibitors of the enzymatic browning reaction. Labuza et al., *Cereal Foods World*, 34(4):353 (1989). However, ficin treatment is detrimental to the texture and quality of foods because ficin's proteolytic activity degrades protein in the foods. For example, a commercial latex extract prepared from fig latex can be used as the starting material. Fig latex extracts contain ficin and other compounds and are referred to as "crude ficin" or "crude ficin extracts". Crude ficin extracts are useful as a source for obtaining Formulae IV, V and VII because these extracts are commercially available. Crude ficin extracts are generally available in solid form, as a powder or tablet. The crude ficin preparations are characterized in that the major protease component is ficin, a protein having a molecular weight of about 20,000 daltons. The presence of ficin can be detected by a method which separates materials based on molecular weight, such as, for example, gel permeation-high performance liquid chromatography (GPC-HPLC), and by the ficin-catalyzed hydrolysis of benzoyl-L-arginine-p-nitroanilide (L-BAPNA), which is a sensitive assay for ficin activity. A method of obtaining Formula IV, V and Formula VII from crude latex or a crude latex extract is set out in Examples 2, 3 and 4, respectively.

Formula I represents several commercially available compounds, such as alkylresorcinols, which have been used for other applications. Applicants have now discovered that compounds having the structure shown as Formula I are effective inhibitors of oxidative browning in many foods susceptible to such browning. For example, 4-hexyl-resorcinol, Formula II, has been used as a medication, and is described in *The Merck Index*, 10th edition, p. 681, Merck & Co., Inc., Rahway, N.H. (1983).

The anti-browning compounds represented by Formulae II and IV–VII can be prepared by synthetic methods.

In one embodiment, Formula V is synthesized according to the following general procedure which is set out in detail in Example 5: 7-hydroxycoumarin is hydrogenated to 7-hydroxydihydrocoumarin, followed by reaction with an excess of diaminobutane to yield Formula V (2,4-dihydroxyphenylpropionyldiaminobutane). The synthesized compound is identical to the compound isolated from the crude ficin extract, as determined by $^1H$ and $^{13}C$ NMR, mass spectral analysis, elemental analysis and TLC.

Figure 5:
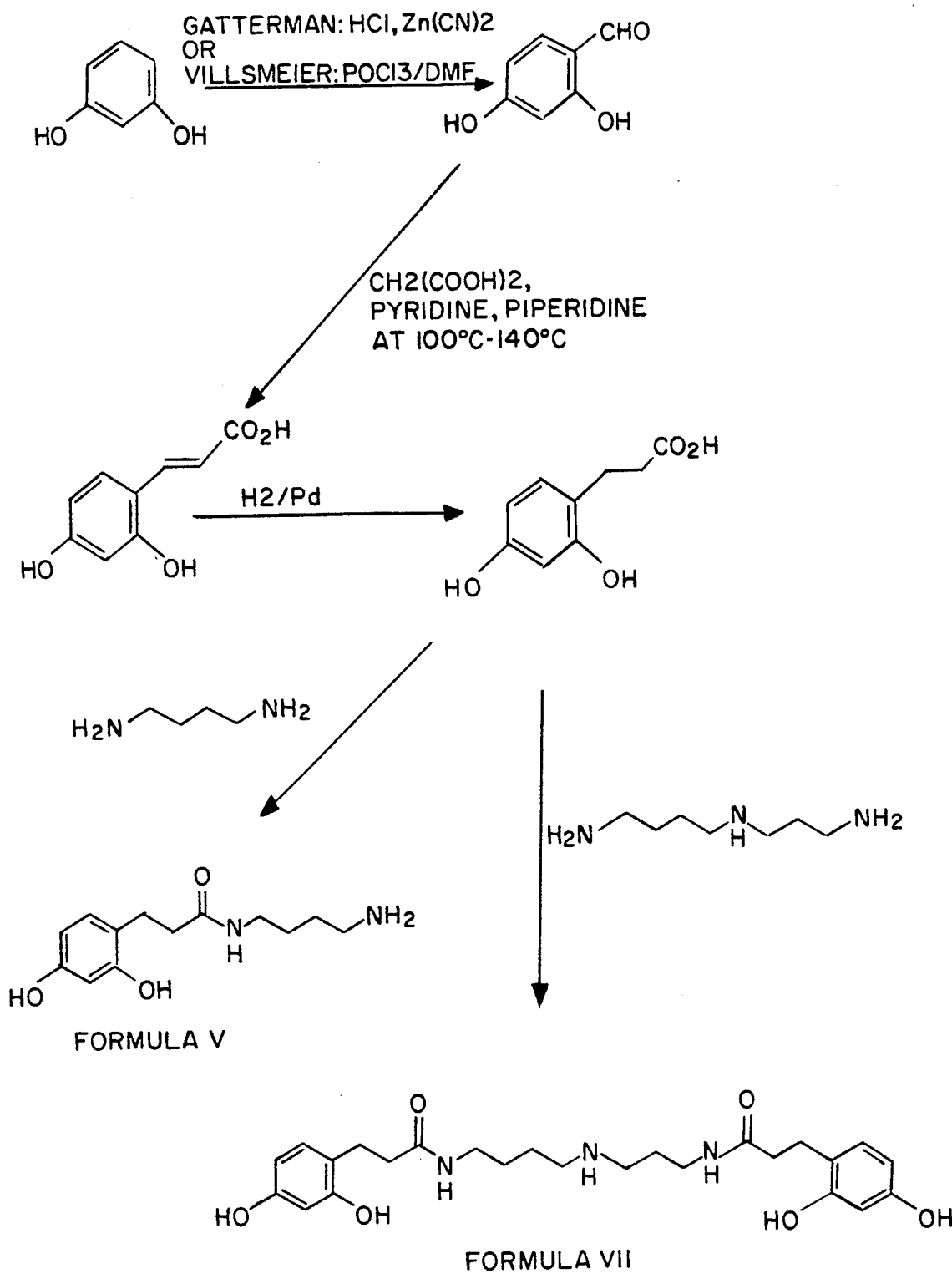
FIG. 5 is a schematic illustration of showing the synthesis steps for the compounds of Formula V and Formula VII.

In another embodiment the compounds of Formulae V and VII can be synthesized according to the following procedure, which is shown schematically in FIG. 5: resorcinol (1,3-dihydroxybenzene) is derivatized by treatment with a reagent which results in the addition of one C atom to an aromatic ring, e.g., Gatterman reagent $(Zn(CN)_2, HCl)$ or Villsmeier reagent $(POC_3/DMF)$, to add an aldehyde group to the ring thereby forming 2,4-dihydroxybenzaldehyde. This compound is further reacted with malonic acid $(CH_2(COOH)_2)$ in a basic organic solvent such as pyridine and piperidine, at an elevated temperature (e.g., about 100° to 140° C.) to yield 2,4-dihydroxycinnamic acid. The double bond in the side chain of 2,4-dihydroxycinnamic acid is hydrogenated, for example using hydrogen and palladium, to form 2,4-dihydroxyphenylpropionic acid. Reaction of this compound with an excess of diaminobutane yields Formula V (2,4-dihydroxyphenylpropionyldiaminobutane), while reaction with spermidine (in the correct molar ratio) yields the bis-phenolic compound, Formula VII (bis-2,4-dihydroxyphenylpropionylspermidine).

The present resorcinol derivatives can be applied to various foods and beverages to prevent or inhibit browning, particularly enzymatic browning. The term "enzymatic browning" as used herein refers to oxidative darkening or discoloration resulting from the formation of o-quinone and quinone polymers which result from the action of PPO in forming quinones or from the polymerization of quinones, and with other components, which occur naturally in foods.

To prevent browning, the resorcinol derivatives are used to treat the food or beverage in an amount or concentration sufficient to inhibit or prevent browning. The form of treatment will depend upon the food or beverage being treated, and the results sought, and can include e.g., dipping, spraying, dusting, sprinkling, immersing, mixing and/or soaking. The compounds can be added to an aqueous diluent, for example, water, salt water or buffer, and applied to the food, or can be added neat, e.g., to fruit juice. The amount needed will depend upon the susceptibility of the food or beverage to browning, the condition of the food and the storage conditions. The amount sufficient to prevent or inhibit browning can be determined empirically by one skilled in the food art.

Figure 10:
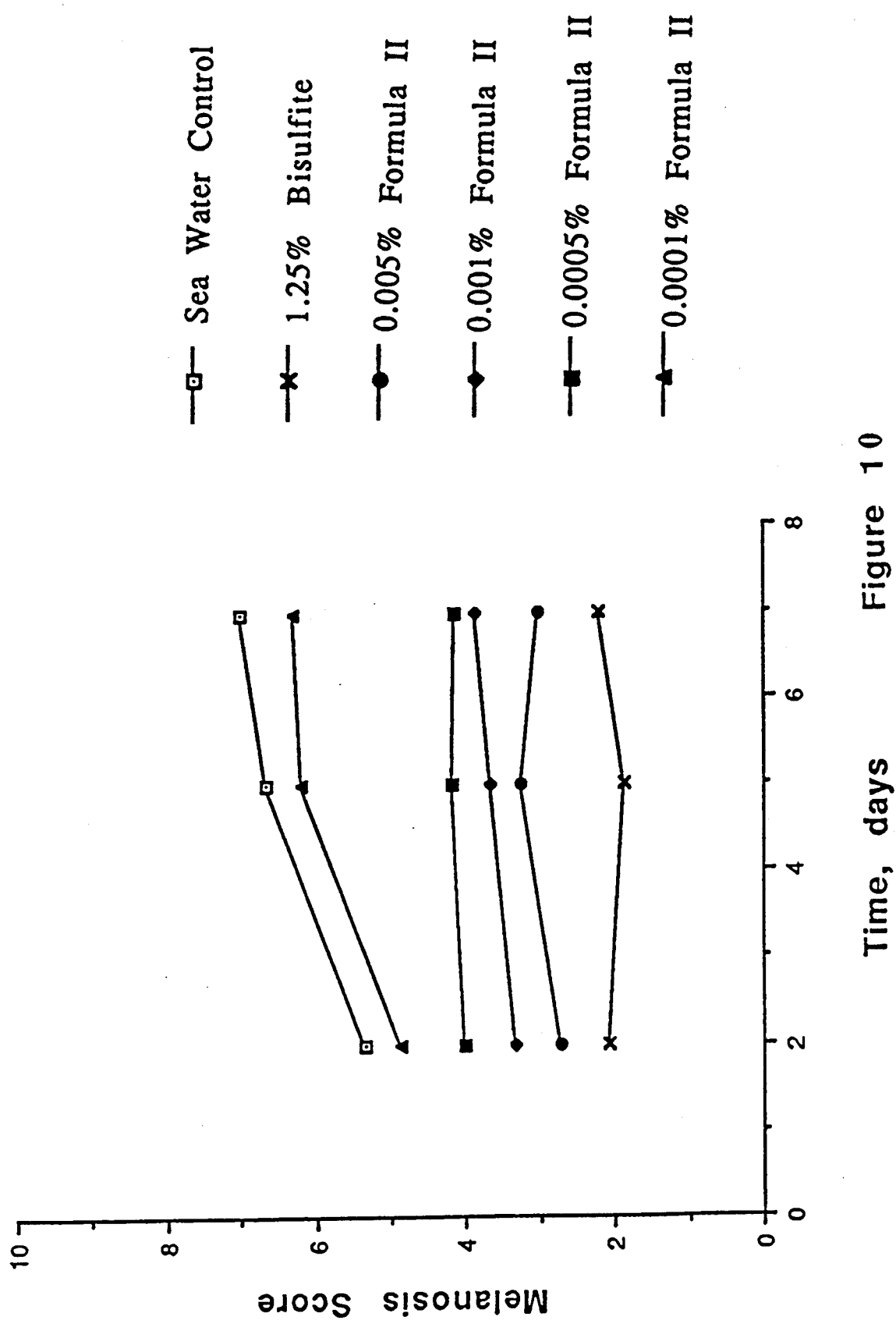
FIG. 10 is a graph comparing the effect of sodium bisulfite, sea water, and various concentrations of the compound of Formula II on the formation of melanosis in pink shrimp.

In one embodiment of the present invention, pink shrimp were treated with an aqueous solution of the compound of Formula II. Formula II was used at concentrations ranging from 0.0001 to 0.005%, and compared to shrimp treated with sodium bisulfite and sea water. The results are shown in FIG. 10. The sea water treated shrimp developed melanosis spots within 1–2 days. Formula II was more effective on a weight basis than sodium bisulfite in inhibiting browning of the shrimp. For example, a solution containing as little as 0.005% by weight of Formula II was almost as effective in inhibiting shrimp melanosis as a solution of 1.25% by weight bisulfite. A concentration of up to about 0.1% of Formula II can be used for inhibiting browning.

Figure 4:
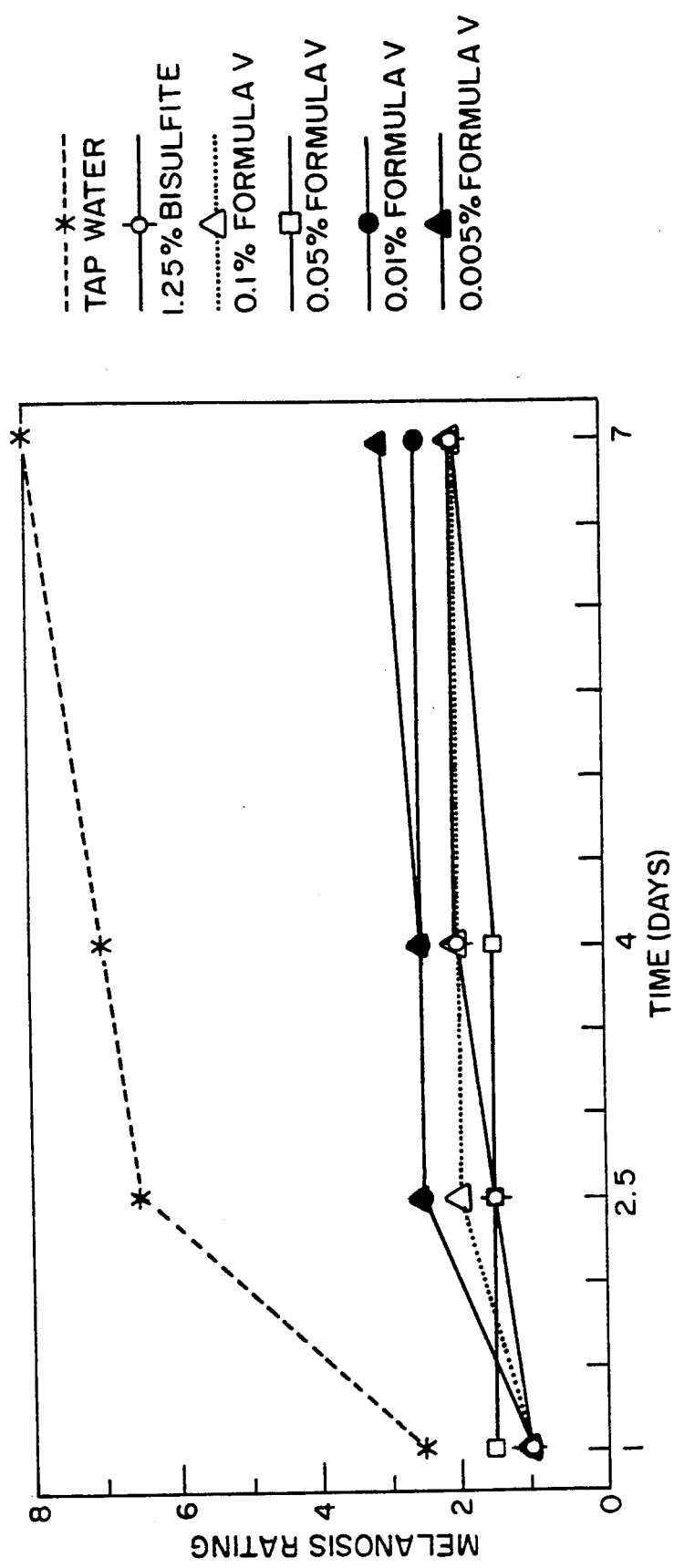
FIG. 4 is a graph comparing the effects of sodium bisulfite and various concentrations of the compound of Formula V on the formation of melanosis in shrimp.

In another embodiment of the present invention, pink shrimp were treated with an aqueous solution of Formula V prepared as described herein. Formula V was used at concentrations ranging from about 0.1% by weight to about 0.001% by weight and compared to shrimp treated with sodium bisulfite, and untreated shrimp. The results are shown in FIG. 4. The untreated shrimp quickly developed black spots (within 1–2 days). Formula V was more effective on a weight basis than sodium bisulfite in inhibiting browning of the shrimp. For example, a solution containing as little as about 0.005% by weight of Formula V was as effective in inhibiting shrimp melanosis as a solution of 1.25% by weight of sodium bisulfite. A concentration of about 0.1% by weight of the present resorcinol derivatives is particularly effective for this purpose.

The compositions and methods of the present invention are useful in preventing or significantly inhibiting browning in many foods and beverages which are susceptible to browning. Such foods and beverages include, but are not limited to, shrimp, potatoes, apples, bananas, lettuce, peaches, wines and some fruit juices. The present composition does not cause degradation of foods, particularly shrimp. Browning is "prevented" if it is completely eliminated. Browning is "significantly inhibited" if browning takes place at a significantly lower rate compared to untreated foods in the same time frame.

The invention is further illustrated by the following examples.

EXAMPLES

EXAMPLE 1

Preparation of YM5 Eluate By Ultrafiltration of Crude Ficin

A 50 mg/mL solution of crude EDC ficin (Enzeco Ficin, Enzyme Development Corp., (EDC) New York, N.Y.) was prepared in 50 mM sodium phosphate, pH 6.5

(Sigma Chemical Co., St. Louis, Mo.) A 5 mL aliquot was filtered with a 0.45μ filter producing a clear filtrate. A subaliquot (2.5 mL) of the filtrate was ultrafiltered using an Amicon 5000 MWCO YM5 membrane (Amicon Corp., Danvers, Mass.). The ultrafiltered eluate is referred to as the "YM5 eluate". The 0.45μ-filtrate and the YM5-ultrafiltered material were analyzed by gel permeation chromatography-high performance liquid chromatography (GPC-HPLC) and found to be free of any absorbance at 214 nm in the retention time range corresponding to ficin. Also, no ficin activity was detected in the YM5 eluate using the chromophoric substrate benzoyl-L-arginine-p-nitro-anilide (L-BAPNA).

Following ultrafiltration, the crude ficin, the 0.45μ filtrate, and the YM5 eluate were assayed for inhibition of polyphenol oxidase (PPO) using the model system described below.

The model assay system consisted of the following reagents:

50 mM sodium phosphate, pH 6.5 (Sigma Chemical Co.);
0.5 mM L-dihydroxyphenylalanine (L-DOPA; Sigma Chemical Co.);
PPO (mushroom, Sigma Chemical Co.);
+/− varying concentrations of the crude EDC ficin; and
YM5 preparations in a 1 mL total volume.

These reagents were combined, and the rate of the reaction determined by monitoring the change in optical density per minute (OD/min.) at 475 nm in a 1 cm pathlength cuvette using a Perkin Elmer UV-VIS spectrophotometer thermostatted to 25° C. Inhibition of PPO activity was assayed by varying the concentration of the crude ficin and YM5 preparations by the addition of varying aliquots of the test solutions to a cuvette containing the PPO and buffer. The cuvette was preincubated at 25° C. for 1 minute and the reaction initiated by the addition of L-DOPA. PPO assays were performed in the absence and presence of each of the ficin preparations and the ficin-free YM5 eluate. All three preparations showed comparable levels of inhibition. Therefore, the inhibition of PPO activity could not be due to the action of ficin on PPO.

EXAMPLE 2

Purification of Melanosis Inhibitor (Formula IV) from Crude Ficin

The crude EDC ficin (50 g) was extracted with 400 mL of methanol. The supernatant was rotary evaporated to dryness. The solid obtained was partially purified by reverse phase HPLC (RP-HPLC).

Reverse phase HPLC is a purification method based on the separation of molecules according to their interaction with a hydrophobic stationary phase within an HPLC column as the hydrophobicity of the mobile phase increases. In this case the stationary phase (column packing) was a resin coated with octadecyl groups ($C_{18}$) and the mobile phase (the solvent which flows through the column) was 0.1% trifluoroacetic acid (TFA) with varied amounts of acetonitrile present. A purification protocol was developed on an analytical scale and then adapted to the preparative scale using a Waters DeltaPrep HPLC system. (Waters Associates, Millipore Corp., Milford, Mass.).

A linear gradient of increasing acetonitrile concentration was developed and the compound eluted at about 20% acetonitrile. The peak inhibitor fraction was pooled and further purified by HPLC using a Waters Delta Pak column (15μ 7.8×30 cm). The eluant was monitored at 214 nm and the fractions were assayed to confirm the presence of the inhibitor. The peak fractions were pooled and concentrated. Samples of the Formula IV compound (isolated as described above or synthesized) were analyzed by several analytical techniques: $^1H$ and $^{13}C$ NMR and mass spectral analysis and the results were consistent with the structure assigned to Formula IV.

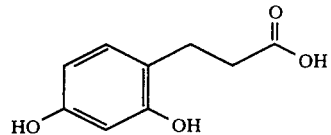

$^1H$ NMR ($CD_3CN$) 300 MHz δ6.89 (d, J=8 Hz, 1H, $C_6$), δ6.27 (d, J=2.81 Hz, 1H, $C_3$), δ6.24 (d of d, J=8.24, 2.59 Hz, 1H, $C_5$), δ2.716 (t, J=7.4 Hz, 2H, $C_8$), δ2.515 (t, J=7.24 Hz, 2H, $C_7$).

$^{13}C$ NMR ($CD_3CN$) 75.47 MHz (J-Modulated spin echo method) δ176.20 ($C_9$), δ157.35 ($C_2$), δ156.41 ($C_4$), δ131.69 (−ve intensity, $C_6$), δ119.43 ($C_1$), δ107.83 (−ve intensity, $C_5$), δ103.57 (−ve intensity, $C_3$), δ34.83 ($C_8$), δ25.50 ($C_7$).

Mass Spectra EI m/s M+ 182, 164 (M+-$H_2O$), 136, 123. Fast atom bombardment (FAB) m/z M+H+ 183, 165 (M+-$H_2O$).

EXAMPLE 3

Purification of Melanosis Inhibitor (Formula V) from Crude Ficin

The YM5 eluate obtained in Example 1 was further purified by ion-exchange chromatography and RP-HPLC. A solution of YM5 eluate obtained as described in Example 1 in 2 mM sodium phosphate (pH 6.5) was loaded onto a column of SP-Sephadex resin (Pharmacia, Uppsala, Sweden). The material which did not adsorb to the resin was washed off by pumping two volumes of 2 mM sodium phosphate (pH 6.5) through the column. A linear sodium chloride gradient (0–0.2 M) was applied to the column which elutes molecules as a function of their strength of interaction with the resin, thereby effecting separation of the previously adsorbed molecules. The eluted material was monitored for absorbance at 214 and 280 nm, and collected in 20 mL fractions. The total gradient volume was two liters. Fractions were tested for the presence of inhibitor using the model assay system described in Example 1. Five peaks of inhibition were found upon analysis. The fractions found under these peaks were pooled, frozen, and lyophilized. Two peaks labeled Pool IV and Pool V appeared to be the most potent inhibitors based on the ratio of % inhibition to peak size, and were chosen for further purification with RP-HPLC, as described in Example 2.

The lyophilized material from SP-Sephadex Pool IV was dissolved in the mobile phase, centrifuged to remove particulates, and loaded onto the HPLC column. A linear gradient of increasing acetonitrile concentration was developed and the inhibitor eluted at about 15% acetonitrile. The eluant was monitored at 214 and 280 nm with a multichannel UV-Vis detector and in certain runs the fractions were assayed to confirm the presence of the inhibitor. The peak inhibitor fractions were pooled, concentrated in a SpeedVac, frozen, and lyophilized. Re-analysis by RP-HPLC in a TFA/methanol gradient system indicated a high degree of purity for the recovered inhibitor.

The purified Pool IV inhibitor was analyzed by several physical methods and chemical tests. A UV-Vis spectrum of the inhibitor showed an absorbance maximum at 280 nm, typically in the wavelength range for an aromatic or phenolic compound. Reaction with bicinchonic acid and ninhydrin indicated the presence of an amide bond and a primary amine, respectively.

Samples of the inhibitor were analyzed by several analytical techniques: $^1H$ and $^{13}C$ NMR and mass spectral analysis. The results were consistant with the structure assigned to Formula V:

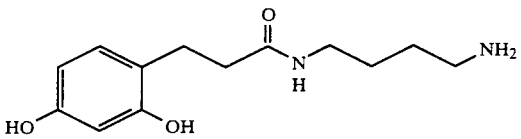

$^1H$ NMR (CD$_3$CN) 300 MHz $\delta$7.5–6.5 (broad, OH), $\delta$6.9–6.8 (b, CONH), $\delta$6.868 (d, J=8.1 Hz, 1H, C$_6$), $\delta$6.304 (d, J=2.3 Hz, 1H, C$_3$), $\delta$6.259 (d of d, J=2.4, 8.0 Hz, 1H, C$_5$), $\delta$5.5–4.8 (b, NH$_2$), $\delta$3.115 (q, J=12.38, 6.23 Hz, 2H, C$_{10}$), $\delta$2.908 (b, 2H, C$_{13}$), $\delta$2.725 (t, J=6.8 Hz, 2H, C$_8$), $\delta$2.439 (t, J=6.8 Hz, 2H, C$_7$), $\delta$1.51, 1.46 (overlapping multiplets, 4H, C$_{11}$, C$_{12}$).

$^{13}C$ NMR (D$_2$O) 75.47 MHz (J-Modulated spin echo method) $\delta$176.68 (C=O), $\delta$155.74 (C$_2$), $\delta$155.41 (C$_4$), $\delta$132.09 (−ve intensity, C$_6$), $\delta$119.59 (C$_1$), $\delta$107.97 (−ve intensity, C$_5$), $\delta$103.49 (−ve intensity, C$_3$), $\delta$39.81 (C$_{13}$), $\delta$39.04 (C$_{10}$), $\delta$36.69 (C$_8$), $\delta$26.33 (C$_7$), $\delta$26.09 (C$_{11}$), $\delta$24.69 (C$_{12}$).

Mass Spectra DCI m/z M+H+ 253, 165 (M-NH(CH$_2$)$_4$NH$_2$) EI m/z M+ 252 164, (C$_9$H$_8$O$_3$) 136, 123, Fast atom bombardment (FAB) m/z M+H+ 253.

EXAMPLE 4

Purification of Melanosis Inhibitor (Formula VII) from Crude Ficin

The lyophilized material from SP-Sephadex Pool V obtained according to the procedure described in Example 2, was further purified by RP-HPLC. The conditions for the purification were the same as those used in Example 2. A linear gradient of increasing acetonitrile concentration was developed and the compound, Formula VII, eluted at about 30% acetonitrile. The eluant was monitored at 214 and 280 nm with a multichannel UV-Vis detector and in certain runs the fractions were assayed to confirm the presence of the inhibitor, represented by Formula VII. The peak inhibitor fractions were pooled and further purified by HPLC using a Waters Delta Pak column (15µ, 7.8×30 cm). The eluant was monitored at 214 nm and the fractions were assayed to confirm the presence of the inhibitor. The peak fractions were pooled and concentrated. Re-analysis of RP-HPLC indicated a high degree of purity for the recovered inhibitor.

Samples of the Formula VII compound were analyzed by several analytical techniques ($^1H$, mass spectral analysis) and were consistent with the assigned structure:

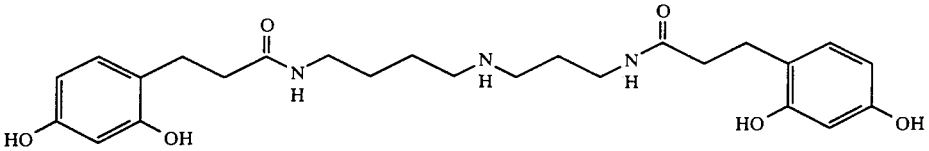

$^1H$ NMR (CD$_3$OD) 300 MHz $\delta$6.861, 6.845 (d, J=8.16 Hz, 2H, C$_6$, C$_{25}$), $\delta$6.276 (overlapping doublets, J=2.56, 2H, C$_3$, C$_{22}$), $\delta$6.208, 6.197 (overlapping d of d, J=8.1, 2.57 Hz, 2H, C$_5$, C$_{24}$), $\delta$3.241, 3.180 (triplets, J=6.30, 4H, C$_{10}$, C$_{16}$), $\delta$2.893–2.711 (well resolved m, 8H, C$_8$, C$_{13}$, C$_{14}$, C$_{18}$), $\delta$2.51, 2.44 (t, J=7.34, 4H, C$_7$, C$_{19}$), $\delta$1.761 (quintet, 2H, C$_{15}$), $\delta$1.601–1.604 (unresolved m, 4H, C$_{11}$, C$_{12}$).

Mass Spectra DCI m/z weak 310 (M-C$_9$H$_8$O$_3$), 165 (C$_9$H$_8$O$_3$H+) 146 (C$_7$H$_{19}$N$_3$H+) EI (high resolution) m/z 309 (M-C$_9$H$_8$O$_3$), FAB m/z M+H+ 474,310 (M-C$_9$H$_8$O$_3$).

EXAMPLE 5

Synthesis of the Formula V Compound

The compound represented by Formula V (2,4-dihydroxyphenylpropionyldiaminobutane):

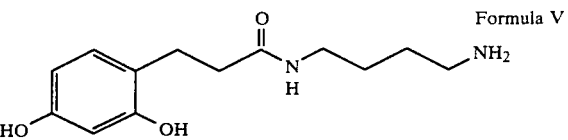

was synthesized according to the following procedure:

A solution of 7-hydroxycoumarin (5.0 g, 0.031 mol; Aldrich Chemical Company) in absolute ethanol (200 mL) was hydrogenated under pressure in a Parr apparatus over 10% Pd/C (Catalyst; 500 mg, 50% water; Kodak Inc., Rochester, N.Y.) for 24 hours at 55° C. Thin layer chromatography (TLC; Silica gel: EtOAc/hexane: 1:1) showed completion of the reaction. The reaction mixture was then filtered over a bed of Celite (Rohm and Haas Co., Philadelphia, Pa.) and evaporated in vacuo to provide the crude product (4.5 g). A portion (2.5 g) of this material was recrystallized from toluene and dried under vaccuum to provide 7-hydroxydihydrocoumarin. Yield: 1.83 g; melting point 133°–135.5° C.;

$^1$NMR (CD$_3$CN) 300 MHz $\delta$7.01 (d, J=8.3 Hz, 1H, C$_5$), $\delta$6.55 (d of d, J=4.1, 2.4 Hz, 1H, C$_6$), $\delta$6.48 (d, J=2.4 Hz, 1H, C$_8$), $\delta$2.847 (t, J=7.2 Hz, 2H, C$_3$), $\delta$2.685 (d of d, J=7.7, 6.0 Hz, 2H, C$_6$).

$^{13}C$ NMR (CD$_3$CN) 75.47 MHz (J Modulatd spin echo method) $\delta$169.85 (C$_2$, +ve intensity), $\delta$157.57 (C$_7$, +ve intensity), $\delta$153.61 (C$_9$, +ve intensity), $\delta$129.72 (C$_5$, −ve intensity), $\delta$157.57 (C$_{10}$, +ve intensity), $\delta$112.21 (C$_6$, −ve intensity), $\delta$104.42 (C$_8$, −ve intensity), $\delta$30.01 (C$_3$, +ve intensity), $\delta$23.35 (C$_4$, +ve intensity).

Diaminobutane (3.0 mL: 0.3 mol; Aldrich Chemical Co.) was warmed to 55° C. under nitrogen in a three-necked flask fitted with an addition funnel. 7-Hydroxydihydrocoumarin (1.0 g, 0.006 mol) in methanol (15 mL) was added dropwise. Upon completion of addition, the reaction mixture was evaporated to dryness and the residue was triturated repeatedly with ethyl acetate. The remaining gum was dried under high vacuum. The material was purified by flash column chromatography [silica; gradient eluent of 20% MeOH/EtOAc/NH4OH (5%) to 30% MeOH/EtOAc/NH4OH (5%)]. The fractions were combined on the basis of TLC to provide Formula V (1.0 g) $^1$-NMR, $^{13}$C-NMR, mass spectra and analytical analysis showed that the synthetic compound was identical to that isolated from the YM5 eluate in Example 3.

$^1$H NMR (CD$_3$CN) 300 MHz $\delta$7.5–6.5 (broad, OH), $\delta$6.9–6.8 (b, CONH), $\delta$6.868 (d, J =8.1 Hz, 1H, C$_6$), $\delta$6.304 (d, J = 2.3 Hz, 1H, C$_3$), $\delta$6.259 (d of d, J=2.4, 8.0 Hz, 1H, C$_5$), $\delta$5.5–4.8 (b,NH$_2$), $\delta$3.115 (q, J=12.38, 6.23 Hz, 2H, C$_{10}$), $\delta$2.908 (b, 2H, C$_{13}$), $\delta$2.725 (t, J=6.8 Hz, 2H, C$_8$), $\delta$2.439 (t, J=6.8 Hz, 2H, C$_7$), $\delta$1.51, 1.46 (overlapping multiplets 4H, C$_{11}$, C$_{12}$).

$^{13}$C NMR (D$_2$O) 75.47 MHz (J-Modulated spin echo method) $\delta$176.68 (C=O), $\delta$155.74 (C$_2$), $\delta$155.41 (C$_4$), $\delta$132.09 (−ve intensity, C$_6$), $\delta$119.59 (C$_1$), $\delta$107.97 (−ve intensity, C$_5$), $\delta$103.49 (−ve intensity, C$_3$), $\delta$39.81 (C$_{13}$), $\delta$39.04 (C$_{10}$), $\delta$36.69 (C$_8$), $\delta$26.33 (C$_7$), $\delta$26.088 (C$_{11}$), $\delta$24.69 (C$_{12}$).

Anal C$_{13}$H$_{20}$N$_2$O$_3$. Calc C 61.88, H 7.99, N 11.11, Found C 61.97, H 7.96 N 11.01.

Mass Spectra DCI m/z M+H+ 253, 165 (M-NH$_2$(CH$_2$)$_4$NH$_2$) EI m/z M+ 252, 164, 136, 123, FAB m/z M+H+ 253.

EXAMPLE 6

Synthesis of the Formula VI Compound

The compound represented by Formula VI (bis-2,4-dihydroxyphenylpropionyldiaminobutane) was synthesized by a modification of the procedure described in Example 5. Diaminobutane (1.09 mL, 5.48 mmoles) was dissolved in 30 mL absolute ethanol. To it was slowly added 7-hydroxydihydrocoumarin (4.5 g). The resulting solution was allowed to stir at room temperature for 1 hour. The solvent was removed by rotary evaporation, resulting in a reddish gum. Addition of excess ethyl acetate followed by rotary evaporation resulted in a pinkish solid which was washed with excess ethyl acetate and then dried in a vacuum desiccator to give 4.6 g (82% yield) of the Formula VI compound. The isolated compound was analyzed by several analytical techniques: $^1$H and $^{13}$C NMR and mass spectral analysis. The results were consistent with the structure assigned to Formula VI.

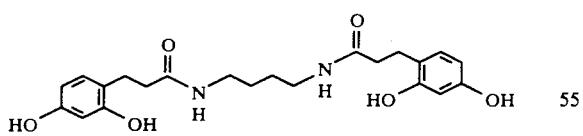

$^1$H NMR (CD$_3$OD) 300 MHz, $\delta$6.841 (d, J=8.1 Hz, 2H, C$_6$, C$_{22}$), $\delta$6.277 (d, J=2.4 Hz, 2H, C$_3$, C$_{19}$), $\delta$6.204 (d of d, J=8.1, 2.4 Hz, 2H, C$_5$, C$_{21}$), $\delta$3.089 (b, 4H, C$_{10}$, C$_{13}$), $\delta$2.779 (t, J=7.4 Hz, 4H, C$_8$, C$_{15}$), $\delta$2.422 (t, J=7.4 Hz, 4H, C$_7$, C$_{18}$), $\delta$1.35 (b, 4H, C$_{11}$, C$_{12}$). $^{13}$C NMR (CD$_3$OD) 75.47 MHz 75.47 MHz (J Modulated spin echo), $\delta$176.05 (C$_9$, C$_{14}$, +ve intensity), $\delta$157.74 (C$_2$, C$_{18}$, +ve intensity), $\delta$157.02 (C$_4$, C$_{20}$, +ve intensity), $\delta$131.58 (C$_6$, C$_{22}$, −ve intensity), $\delta$119.55 (C$_1$, C$_{17}$, +ve intensity), $\delta$107.47 (C$_5$, C$_{21}$, −ve intensity), $\delta$103.59 (C$_3$, C$_{19}$, −ve intensity), $\delta$39.49 (C$_8$, C$_{15}$, +ve intensity), $\delta$37.73 (C$_{10}$, C$_{13}$, +ve intensity), $\delta$27.54 (C$_{11}$, C$_{12}$, +ve intensity), $\delta$27.01 (C$_7$, C$_{16}$, +ve intensity).

Mass Spectra FAB m/z M+H+ 417, 309 (M+-C$_6$H$_5$O$_2$), 253 (M+=C$_9$H$_9$O$_3$).

EXAMPLE 7

Inhibition of PPO By Various Resorcinol Derivatives

In order to determine the effect of various resorcinol compounds on the inhibition of PPO (mushroom), a linear spectrophotmetric assay system similar to that described in Example 1 was used. The assay mixture consisted of:

5 mM sodium phosphate, pH 6.5;

0.133 mM L-dihydroxyphenylalanine (L-DOPA); PPO (mushroom); and

+/− varied concentrations of the compound to be tested

The rate of the reaction was monitored by measuring the change in absorbance per minute at 475 nm at 25° C. The apparent inhibition constants (I$_{50}$) are shown in Table 1.

TABLE 1

| Compound | I$_{50}$, $\mu$M |
|---|---|
| Resorcinol | 2700 |
| Formula II | 0.5 |
| Formula IV | 25 |
| Formula V | 5 |
| Formula VI | 5 |
| Formula VII | 5 |
| 4-Ethylresorcinol | 0.8 |
| 4-n-Propylresorcinol | 1.8 |
| 4-Dodecylresorcinol | 0.3 |
| 4-Cyclohexylresorcinol | 0.2 |
| 4-Hexanoylresorcinol | 750 |
| 4-Carboxyresorcinol (2,4-Dihydroxybenzoic Acid) | 150 |

I$_{50}$ represents the concentration of inhibitor necessary to obtain fifty (50%) percent inhibition of the enzyme. The results show that much lower concentrations of the resorcinol derivatives were needed to reach the same level of inhibition compared to resorcinol.

EXAMPLE 8

Effect of YM5 Eluate on Pink Shrimp Melanosis

Pink shrimp (*Penaeus duorarum*) were caught and frozen in Key West, Fla., and thawed prior to treatment. Melanosis was rated in the shrimp according to the scale developed to describe melanosis shown in Table 2.

TABLE 2

| Scale used to describe and rate the occurrence of melanosis (blackspot) on pink shrimp. Melanosis Scale | |
|---|---|
| 0 | Absent |
| 2 | Slight, noticeable on some shrimp |
| 4 | Slight, noticeable on most shrimp |
| 6 | Moderate, noticeable on most shrimp |
| 8 | Heavy, noticeable on most shrimp |
| 10 | Heavy, totally unacceptable |

The melanosis scale can be related to existing recommendations developed by the National Marine Fisheries Service for grading raw shrimp Code of Federal Regulations (1982) Title 50, part 265, Subpart A, United States General standards for Grades of Shrimp, pp. 262–268. A scale rating of 4 or greater represents a measurable defect in product quality. A rating of 8 or greater would represent a severe defect approaching an unacceptable product.

Harvests were arranged such that fresh, heads-on pink shrimp were obtained within less than 12 hours post-harvest at the dock. All shrimp were routinely washed on-board and temporarily stored in ice. The basic procedure was to rinse 400–600 grams of shrimp in 2.5 liters of variable dip compositions and concentrations for 1 minute then drain and package in plastic bags to be stored in ice. The bags were considered necessary to eliminate the variable influence of melting ice. Iced containers with packaged shrimp were stored in 35° F. (1.7° C.) refrigeration with reicing every other day.

Development of melanosis was scored and photographed routinely during 2 weeks of storage. The bags of shrimp had been numbered such that the investigator could not distinguish amongst the various treatments. One experienced investigator did all scoring relative to the aforementioned scale (Table 2). The scale was accompanied by pre-developed color prints depicting common examples of the advancing stages for melanosis. The intent was to screen for obvious differences between treatments, thus selecting the best treatments for subsequent tests with statistical evaluations.

The various dips or chemical treatments included tap water as a control, sodium bisulfite at a concentration of 1.25%, crude EDC ficin and the YM5 eluate prepared according to the procedure outlined in Example 1, which is designated "F100". The dip solution was fresh tap water.

The treatment (dips) and ratios of shrimp to dip solution are shown in Table 3.

TABLE 3

| Dip Solution | Shrimp to Dip Ratio Vol./Vol. |
| --- | --- |
| Control I (tapwater) | 1/5 |
| Control II (tapwater) | 1/1 |
| BIS (Sodium bisulfite) | 1/5 |
| Ficin, tablet form | 1/5 |
| F1p, ficin powder vial I | 1/1 |
| F2p, ficin powder vial II | 1/1 |
| F100, YM5 eluate (1/5 thru 1/20 dilution with or without buffer B) | 1/2 |

The treatments contained variable additions to tap water, unless otherwise specified in batches made with distilled water. All treatments were complete submergence of the shrimp in the dips for 60 to 80 seconds followed by brief (5–10 seconds) colander drain with mild agitation.

Figure 2:
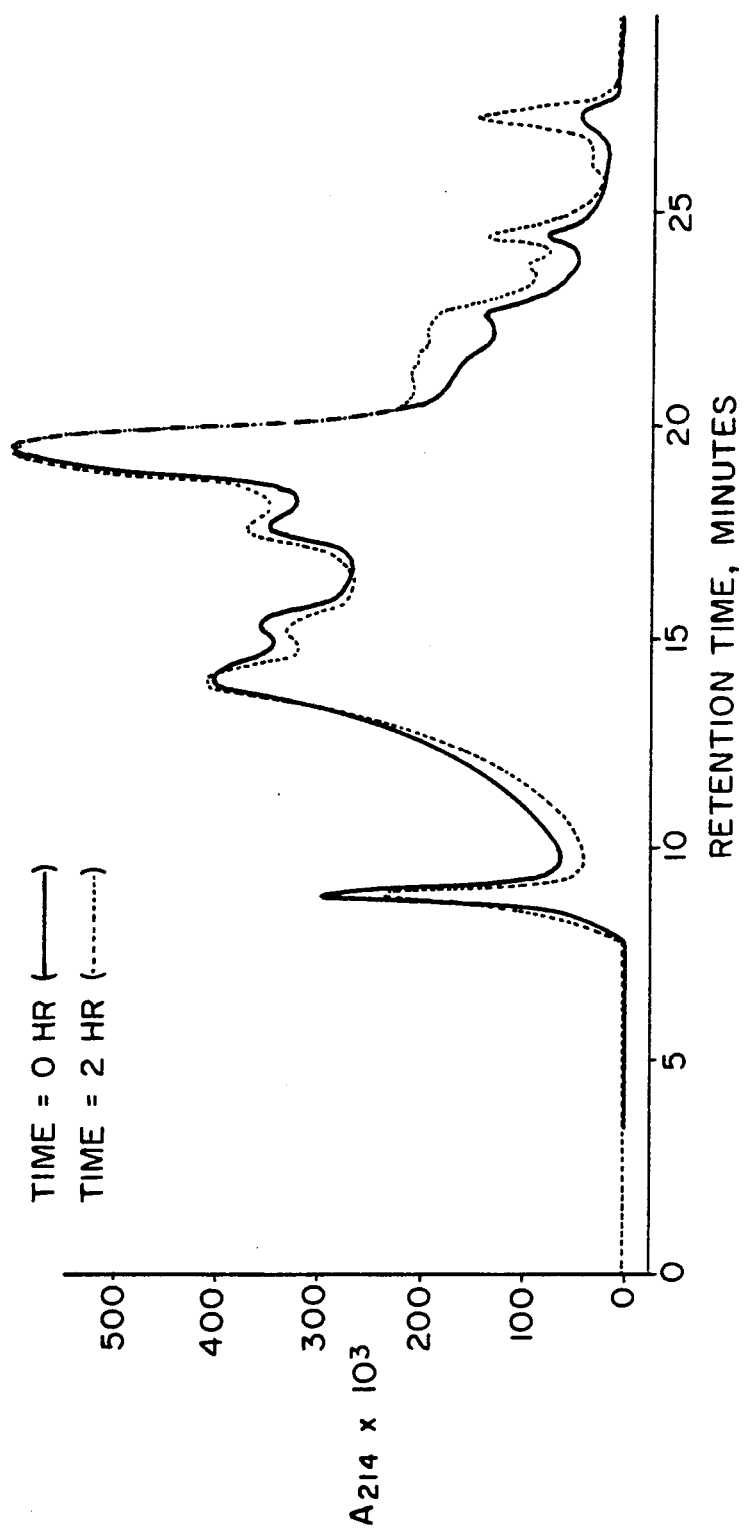
FIG. 2 is a graph comparing the effects of sodium bisulfite, various concentrations of ficin and a YM5 extract (F100) on the formation of melanosis in shrimp.

The results are shown in FIGS. 1 and 2 FIG. 1 shows that the YM5 eluate, F100, was as effective as, or better than, sodium bisulfite in reducing melanosis. FIG. 2 shows that F100 was as effective as crude ficin and more effective than sodium bisulfite in reducing melanosis.

EXAMPLE 9

Inhibition of Enzymatic Browning of Apples by YM5 Eluate

Fresh, whole McIntosh apples, held at ambient temperature (22° to 24° C.) were sliced into quarters, cored and cut into ¼ inch slices. The apple slices were treated by brushing the sliced surfaces or dipping the slices by totally immersing them for various time periods: less than 5 seconds, 10 seconds 1 minute, 2½ minutes and 5 minutes, with the solutions shown in Table 4. Following treatment, the apple slices were allowed to stand at ambient temperature, exposed to air. The slices were checked visually for browning after 0, 1, 2, 3, 4 and 24 hours.

TABLE 4

Apple Treatments
Controls 1) no liquid, i.e., air only
2) deionized water, pH 5.8
3) 50 mM, sodium phosphate buffer, pH 6.7
4) 50 mM, phosphate buffer, pH 2.7 (raised from pH 2.0 using 4.0 N NaOH)

Experimental

5) YM5 eluate, pH 6.3, about 100 mg/mL, prepared as described in Example 1 from (200 mg/mL) crude ficin in sodium phosphate
6) YM5 eluate final pH 4 6, about 100 mg/mL, prepared as described in Example 1 from (200 mg/mL) crude ficin in phosphate buffer (50 mM), pH 2.7 (raised from pH 2.0 using 4.0N NaOH)

The results showed that treatments 5 and 6 (Table 4) using the YM5 eluate minimized the extent of browning of the apple slices. All samples were initially (time 0) white in color. Browning of the controls (treatments 1 through 4, Table 4) was observed after 1 hour, with maximum browning occurring after about 3 hours. After 3 hours, no significant browning was observed in slices receiving treatments 5 and 6. After 24 hours, the slices which received treatments 5 and 6 were slightly browned, but exhibited significantly less browning than the controls.

EXAMPLE 10

Inhibition of Browning in Apples by the Compound of Formula V and YM5 Eluate

Two fresh and unbruised whole McIntosh apples, held at ambient temperature, were sliced with a stainless steel paring knife into quarters, cored, then cut into ¼-inch slices. A volume of 0.8 mL of each of the treatment solutions listed in Table 5 at ambient temperature was applied onto the top exposed surface of freshly cut white slices, triplicate samples per treatment. The Formula V compound was synthesized as described in Example 5. Following application, the slices stood at ambient temperature, exposed to air and light, for periodic visual observation of relative rate and extent of browning, from 15 minutes to 4 hours.

TABLE 5

Apple Treatments
At controlled pH: 6.7–7.0

1) Sodium phosphate Buffer (5 mM)
2) Sodium phosphate Buffer (5 mM) + Lactose* (9.0%)
3) Sodium phosphate Buffer (5 mM) + Lactose* (9.0%) + YM5 (1.0%; without lactose)
4) Sodium phosphate Buffer (5 mM) + Lactose* (9.0%) + Formula V, 0.5% by wt, (20 mM)
5) Sodium phosphate Buffer (5 mM) + Lactose* (9.0%) + 1,4-Diaminobutane, 50 mL/100 mL, (5 mM)
6) Sodium phosphate Buffer (5 mM) + Formula V, 0.5%, (20 mM)
7) Air only.

*Lactose was added due to its presence in the crude ficin preparation which was diluted with lactose solids by the suppliers.

All freshly cut samples initially were white in color. Within 15 minutes after treatment, some browning occurred in all samples except those treated with solutions 3, 4, and 6 which remained white. After one hour, samples treated with 4 and 6 were still white, while the other samples showed a varying extent of browning. The extent of browning of the other samples, in order of least browned to the most browned were 3<2, 5<1, 7. After about 3 hours, maximum extent of browning occurred in samples 1, 2, 3, 5 and 7, ranked as noted above after 1 hour. Samples treated with solutions 4 and 6 remained white and essentially unchanged in color.

Under the examined conditions, the compound of Formula V at a concentration of 20 mM inhibited browning of apples more effectively than the YM5 eluate and crude ficin. Lactose and/or 1,4-diaminobutane did not prevent browning.

EXAMPLE 11

Effect of the YM5 Eluant and the Formula V Compound on Pink Shrimp Melanosis

Pink shrimp (*Penaeus duorarum*) were caught and frozen in Key West, Fla. and thawed prior to treatment. Melanosis was rated in the shrimp according to the scale developed to describe melanosis, as shown in Example 8, Table 2.

The basic procedure was to rinse the shrimp in variable dip compositions and concentrations for 1 minute (for test solutions containing the two highest concentrations of the Formula V compound, i.e., 0.1% and 0.05%, due to lack of sufficient material, the test solution was painted onto 6 individual shrimp), then drain and package in plastic bags to be stored in ice. The bags were considered necessary to eliminate the variable influence of melting ice. Iced containers with packaged shrimp were stored in 35° F. (1.7° C.) refrigeration with reicing every other day. Development of melanosis was scored and photographed routinely during 7 days of storage as described in Example 8.

Figure 3:
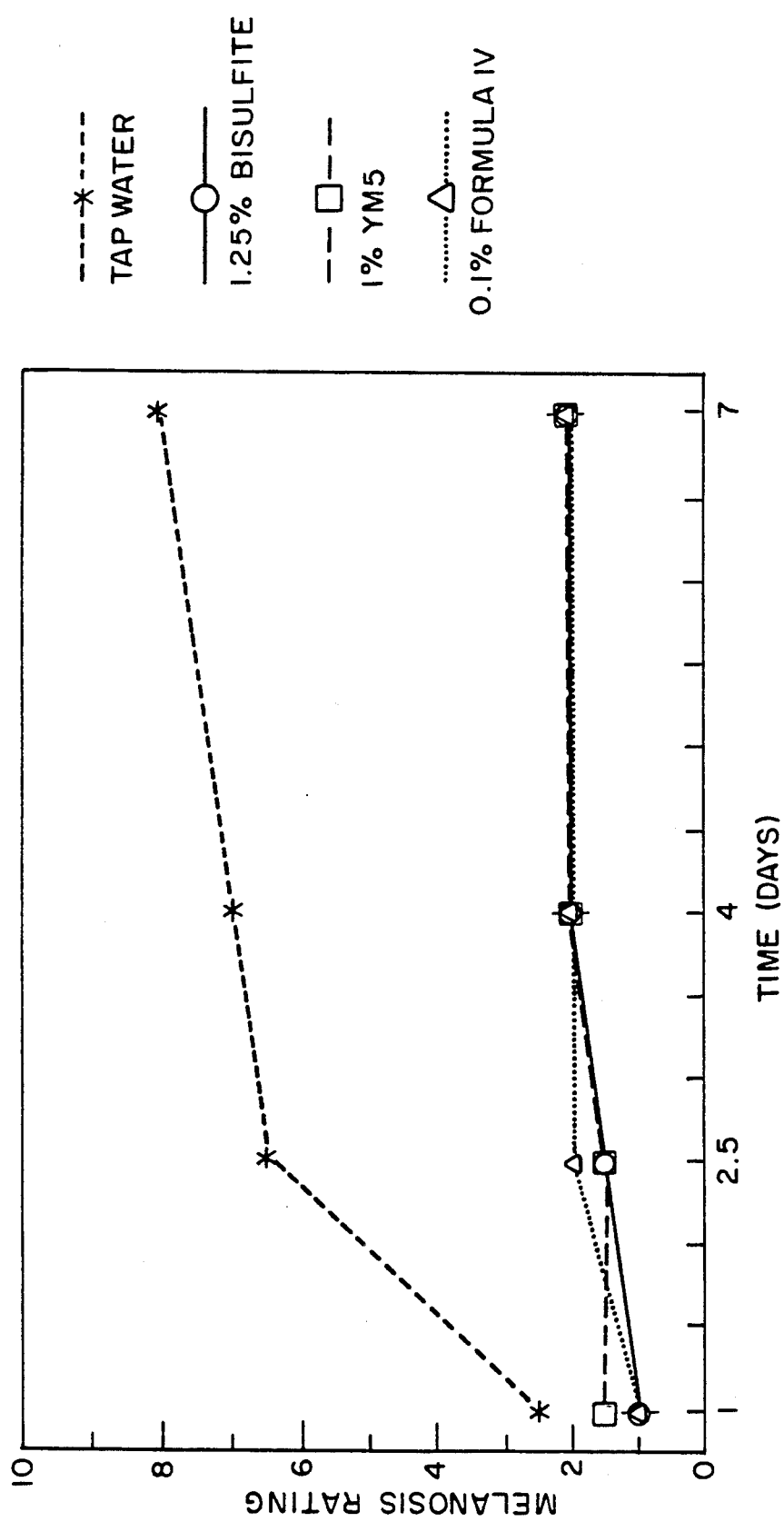
FIG. 3 is a graph comparing the effects of sodium bisulfite, a YM5 extract (1% by wt.) and the compound of Formula V (0.1% by wt.) on the formation of melanosis in shrimp.

The various dips or chemical treatments included tap water as a control, sodium bisulfite at a concentration of 1.25%, YM5 eluant (prepared according to Example 1) at a concentration of 1%, and varying concentrations of the Formula V compound as indicated in FIGS. 3 and 4. The results shown in FIG. 3 show that the compound of Formula V at a concentration of 0.1% by weight was as effective as bisulfite in reducing melanosis. FIG. 4 shows that as little as 0.005% of the Formula V compound was as effective as sodium bisulfite in reducing melanosis.

EXAMPLE 12

Effect of the Formula V Compound on Fresh Pink Shrimp Melanosis

Figure 6:
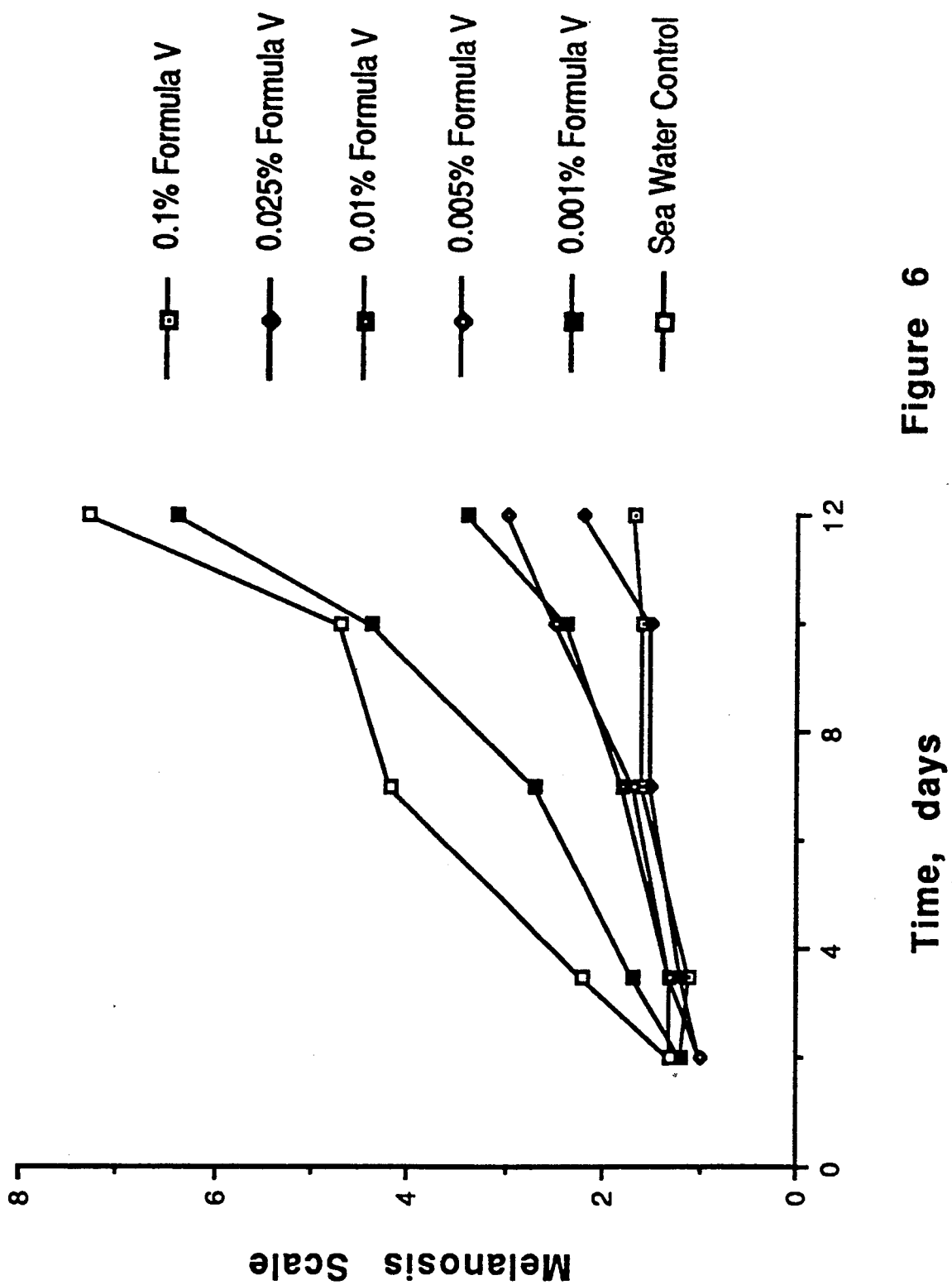
FIG. 6 is a graph comparing the effects of various concentrations of the compound of Formula V on the formation of melanosis in fresh pink shrimp; that is, shrimp which were not frozen prior to treatment.

Pink shrimp (*Penaeus duorarum*) were treated and evaluated as described in Example 8 except that the experiment was carried out on a shrimp boat with freshly caught shrimp. The shrimp were not frozen prior to treatment with various concentrations of the compound of Formula V. All solutions were prepared in sea water. The results are shown in FIG. 6. The Formula V compound is effective in the prevention of fresh pink shrimp melanosis.

EXAMPLE 13

Effect of Post-treatment Rinse on the Performance of the Formula V

Figure 7:
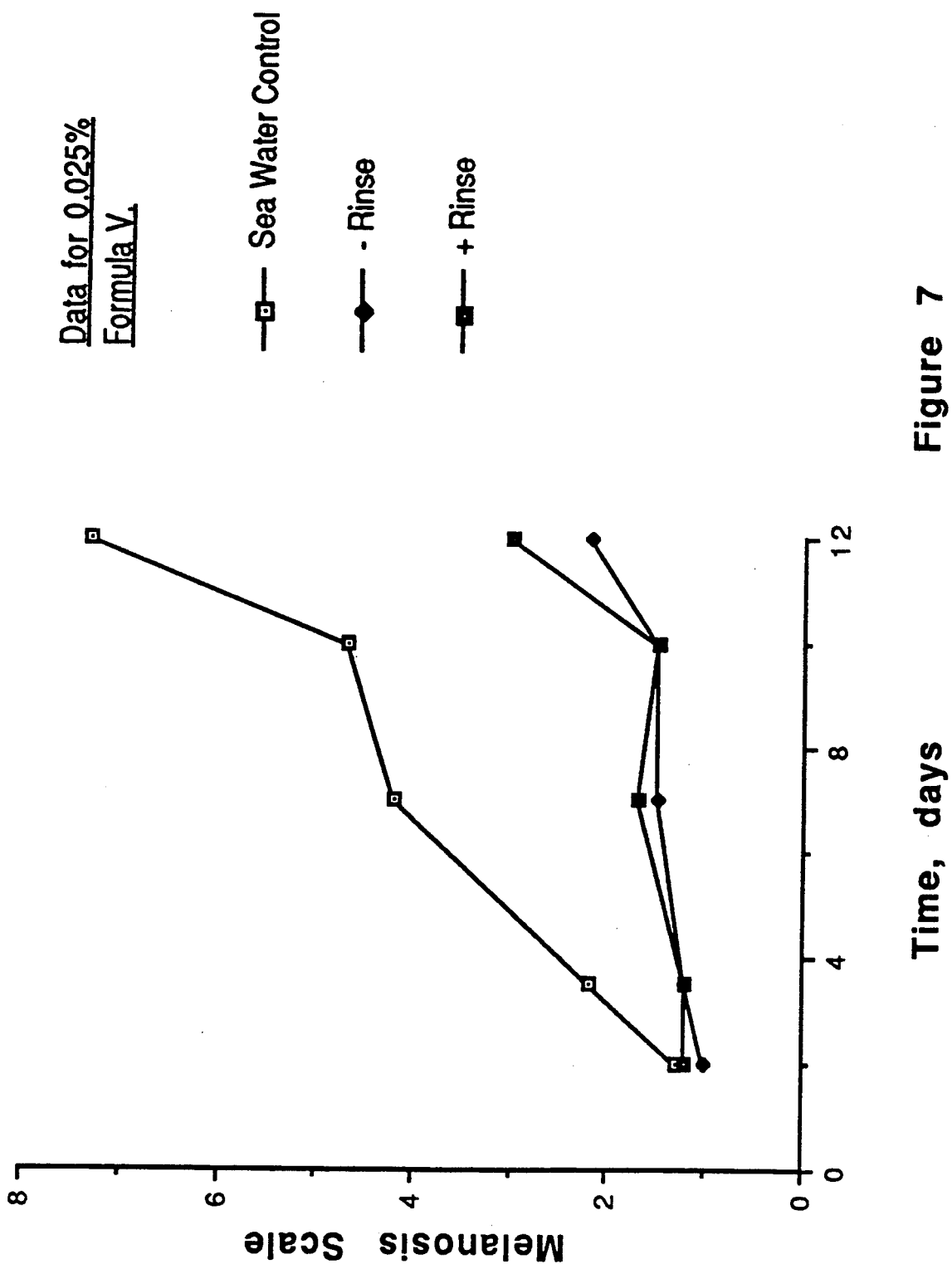
FIG. 7 is a graph comparing the effect of no rinse and a post-treatment sea water rinse on the inhibition of shrimp melanosis by 0.025% of the compound of Formula V.

Fresh pink shrimp were treated and evaluated as described in Example 12. The shrimp treated with 0.025% of the compound of Formula V were stored directly or following a sea water rinse, post-treatment. The result is shown in FIG. 7 and shows that a post-treatment rinse has no significant effect on the inhibition of shrimp melanosis by the compound of Formula V.

EXAMPLE 14

Figure 8:
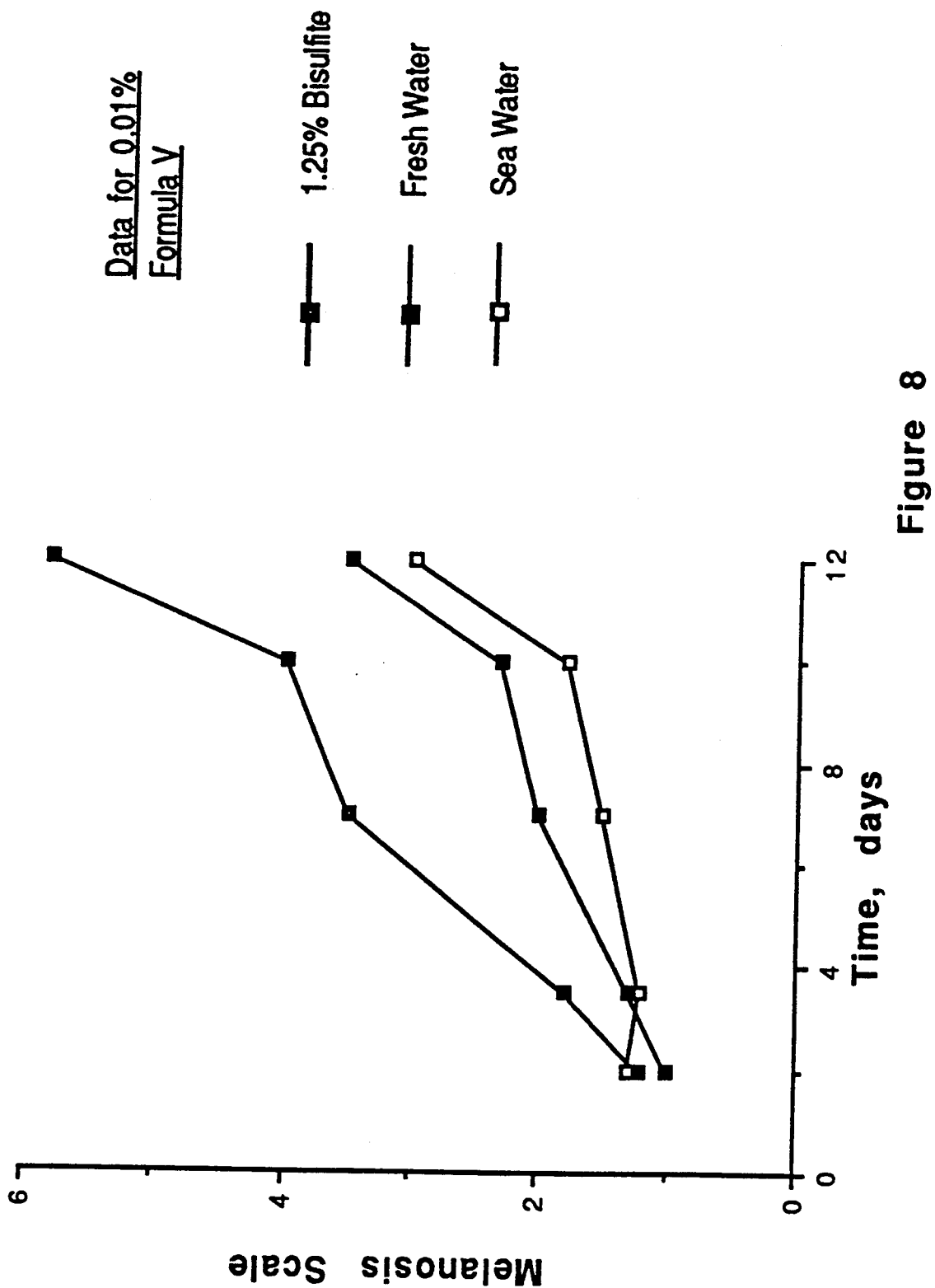
FIG. 8 is a graph comparing the inhibition of shrimp melanosis by a sea water or fresh water solution of 0.01% the compound of Formula V.

The Effect of the Use of Sea Water or Fresh Water as Solvent for Formula V Compound Solutions Fresh pink shrimp were treated and evaluated as described in Example 12. The shrimp were dipped in a 0.01% solution of the compound of Formula V made up in either sea or fresh water. The data is presented in FIG. 8 and shows that there is no significant effect on the inhibition of shrimp melanosis by the Formula V compound when the solutions are prepared in fresh or sea water.

EXAMPLE 15

The Effect of Repeated Dips of Shrimp Into 0.01% of the Formula V Compound

Figure 9:
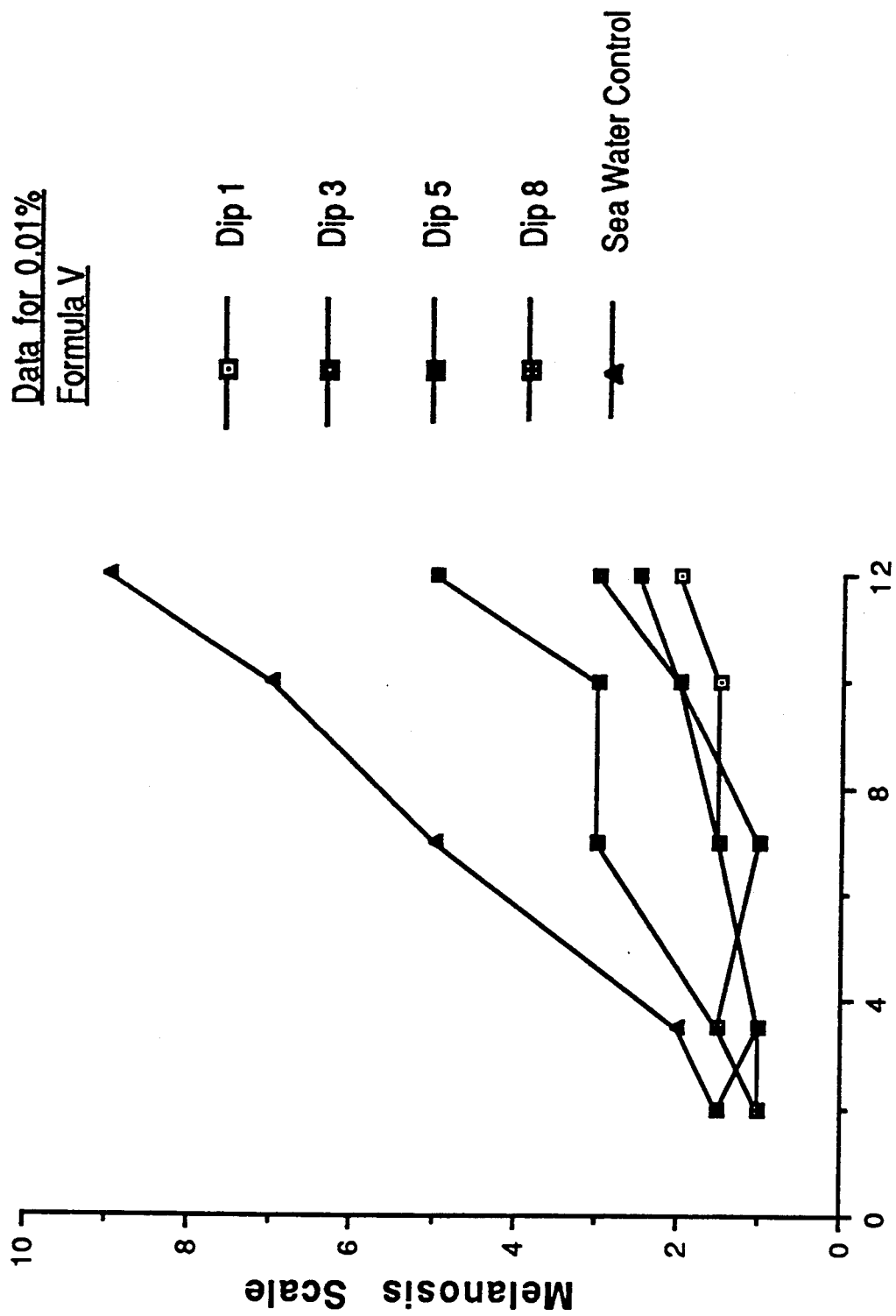
FIG. 9 is a graph comparing the inhibition of shrimp melanosis upon repeated dips of different one pound batches of untreated shrimp into the same one liter of 0.01% the compound of Formula V solution in sea water.

Fresh pink shrimp were treated and evaluated as described in Example 12. In this example, different one pound batches of shrimp were dipped into the same one liter solution of 0.01% of the Formula V compound for one minute each. A total of eight dips were performed. The results are presented in FIG. 9 and show that the Formula V compound is still an effective melanosis inhibitor even after eight dips into the same 0.01% solution.

EXAMPLE 16

The Effect of 4-Hexylresorcinol on the Development of Shrimp Melanosis

Pink shrimp were treated and evaluated as described in Example 8 except that the compound of Formula II (4-hexylresorcinol, Sigma Chemical Co.) was substituted for the Formula V compound. Pink shrimp were dipped into solutions of 0.0001-0.005% of the Formula II compound and stored as described above. The data is graphed in FIG. 10 and shows the Formula II compound to be a potent inhibitor of the formation of shrimp melanosis at concentrations as low as 0.0005%.

EXAMPLE 17

The Effect of the Formula VI Compound on the Development of Shrimp Melanosis

Figure 11:
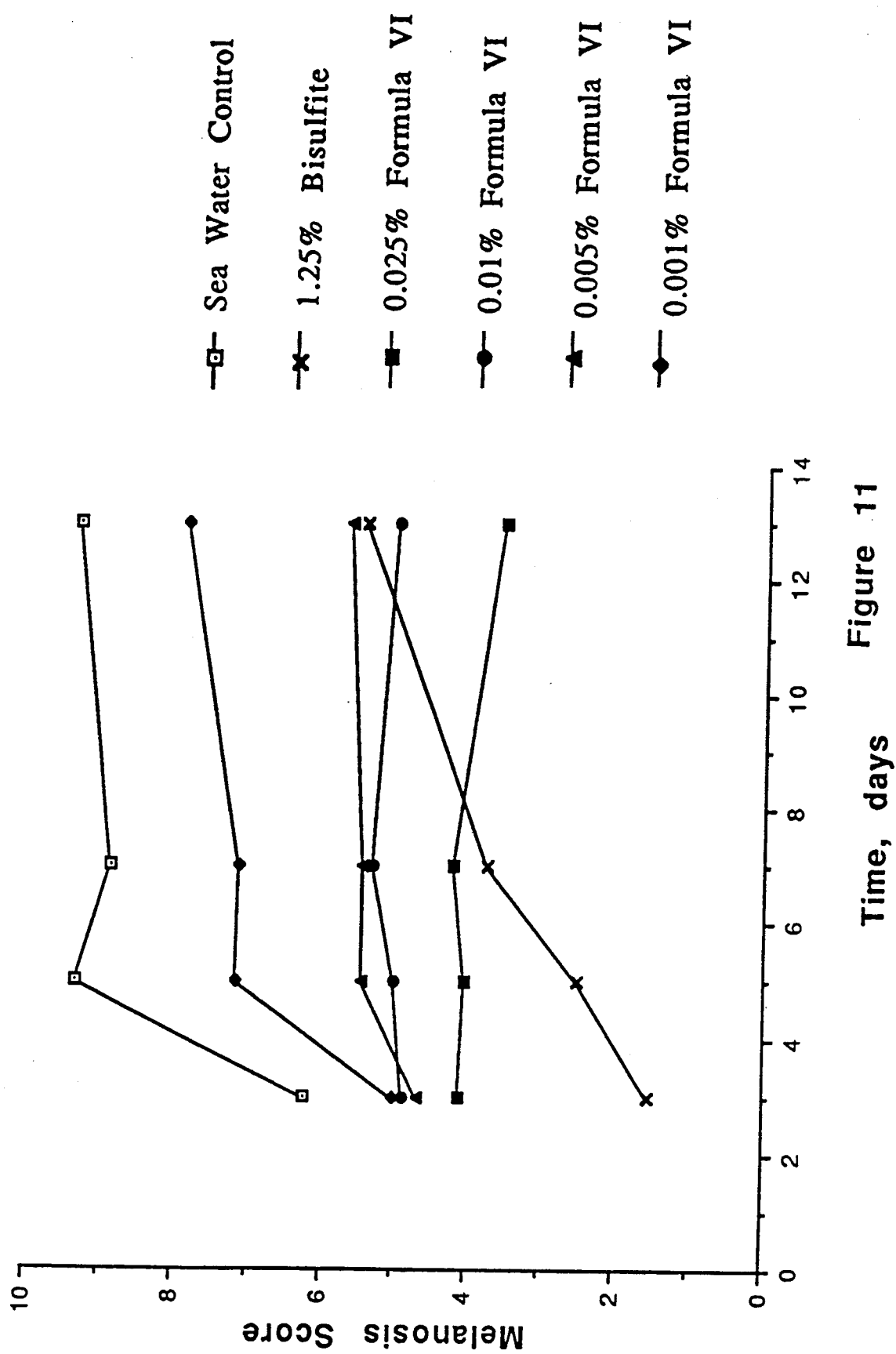
FIG. 11 is a graph comparing the effect of sodium bisulfite, sea water, and various concentrations of the compound of Formula II on the formation of melanosis in pink shrimp.

Pink shrimp were treated and evaluated as described in Example 8 except that the compound of Formula VI (see Example 6) was substituted for the Formula V compound. Pink shrimp were dipped into solutions of 0.001-0.025% of the Formula VI compound and stored as described above. The data is shown graphically in FIG. 11 and shows the Formula VI compound to be a potent inhibitor of the formation of shrimp melanosis at concentrations as low as 0.005%.

EXAMPLE 18

Figure 12:
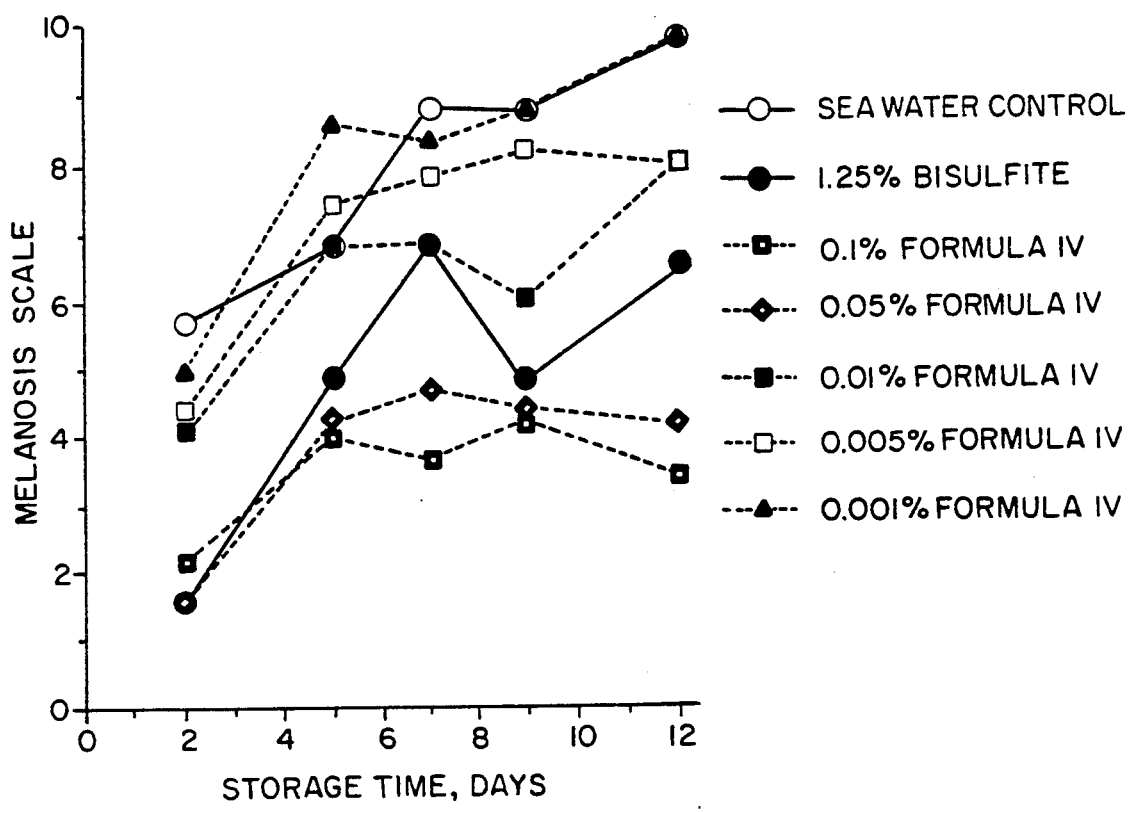
FIG. 12 is a graph comparing the effect of sodium bisulfite, sea water, and various concentrations of the compound of Formula IV on the formation of melanosis in pink shrimp.

The Effect of the Formula IV Compound on the Development of Shrimp Melanosis Pink shrimp were treated and evaluated as described in Example 8 except that the compound of Formula IV (2,4-dihydroxyphenylpropionic acid) was substituted for the Formula V compound. Pink shrimp were dipped into solutions of 0.001-0.1% the Formula IV compound and stored as described above. The data is shown graphically in FIG. 12 and shows the Formula IV compound to be an inhibitor of the formation of shrimp melanosis at concentrations as low as 0.05%.

EXAMPLE 19

Effect of the Formula V Compound on Fresh Brown Shrimp Melanosis

Figure 13:
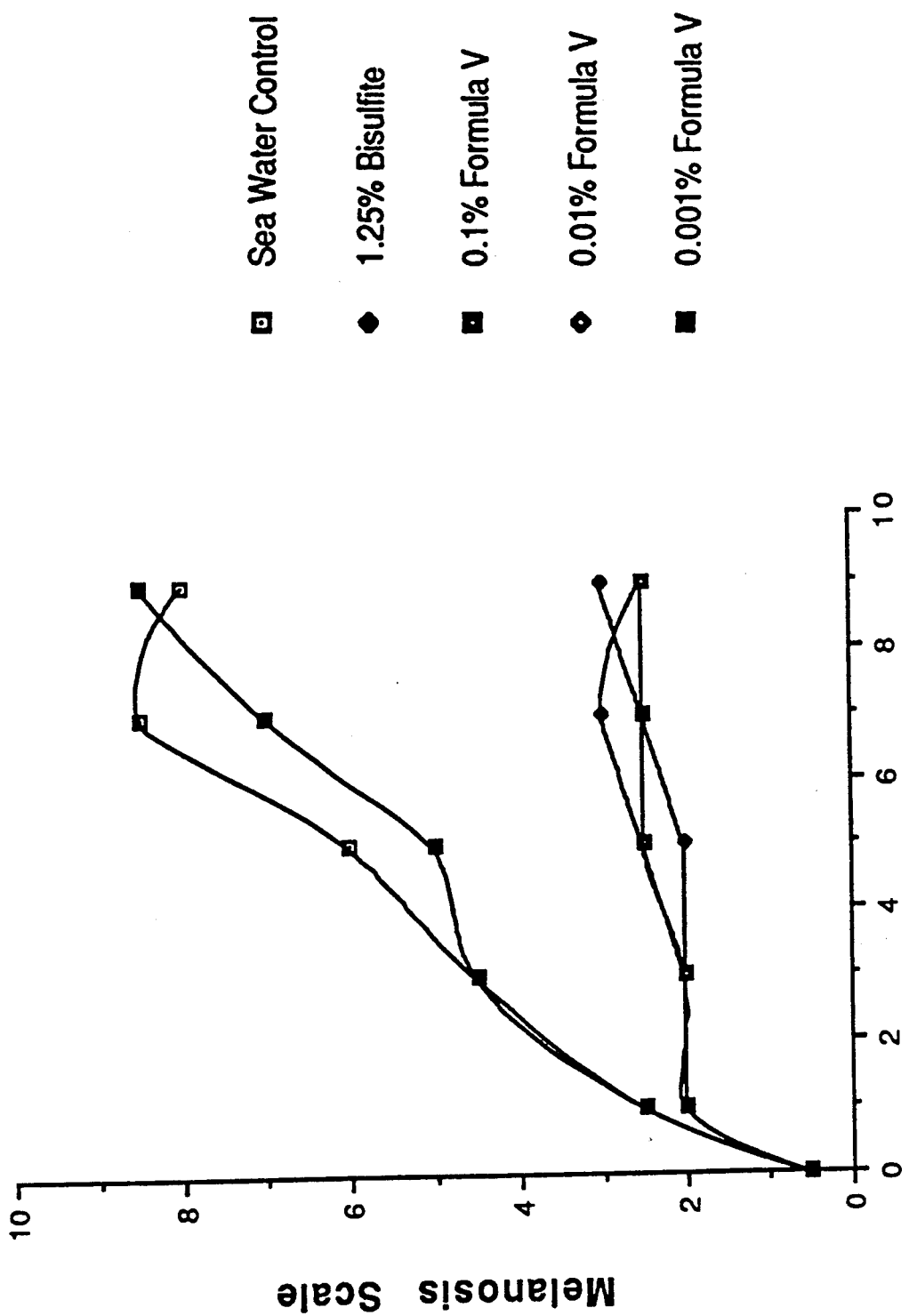
FIG. 13 is a graph comparing the effect of sodium bisulfite, sea water, and various concentrations of the compound of Formula V on the formation of melanosis in Texas brown shrimp.

Brown shrimp were treated and evaluated as described for pink shrimp in Example 8. The results shown in FIG. 13, indicate that the compound of Formula V is as effective in inhibiting melanosis development in brown shrimp as in pink shrimp.

EXAMPLE 20

Effect of the Formula V Compound on PPO Isolated from Tiger Shrimp

PPO was isolated from Taiwanese Black Tiger Shrimp (*Penaeus monodon*) according to the following procedure: Tiger shrimp heads were frozen in liquid nitrogen and then ground to a fine powder. The powdered shrimp heads were extracted into phosphate buffer by stirring. The crude extracts were subjected to ammonium sulfate precipitation between 0–40% ammonium sulfate saturation and subsequently purified by preparative hydrophobic interactive on Phenyl-Sepharose CL-4B (Pharmacia) at 4° C. Purified PPO fractions were concentrated via ultrafiltration. The purity of the enzyme was evaluated using gel electrophoresis. Laemmli, U. K., *Nature*, 227:680-685 (1970).

A control run was made as follows: A 50 μl aliquot of 5 mM sodium phosphate (pH 6.5) was added to 880 μl of 5 mM L-DOPA, 5 mM sodium phosphate (pH 6.5). 70 μl of Tiger shrimp PPO (6.3 mg total protein stock solution) were added and the reaction was immediately monitored using a Beckman DU Spectrophotometer, at 475 nm for 10 minutes, at 35° C.

To test the inhibitor, a 50 μl aliquot of the compound of Formula V (20 mM) prepared as described in Example 5. was added to 880 μl of L-DOPA. 70 μl of Tiger Shrimp PPO (6.3 mg total protein stock solution) were added and the reaction immediately monitored spectrophotometrically as described above for the control. Each test was run in triplicate.

The results are shown in Table 6:

TABLE 6

| Treatment | Reaction Rate (Δ475 nm/min) | Activity |
|---|---|---|
| Control | $1.83 \times 10^{-3} \pm 1.5 \times 10^{-4}$ | 100 |
| 1 mM Formula V | $1.5 \times 10^{-4}$ | 8 |

The results show substantial inhibition of PPO activity by the compound of Formula V.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for inhibiting enzymatic browning of foods or beverages susceptible to such browning, comprising applying to the foods or beverages an amount of a resorcinol derivative sufficient to inhibit the browning of the foods, wherein the resorcinol derivative has the following general formula:

Formula I wherein $R_1$ and $R_2$ are independently selected from the group consisting of: H, $CH_3$, COR', CR', $PO_3R'R''$, and $SO_3R'R''$ wherein R' and R'' are independently H or an alkyl group having from 1 to 6 carbon atoms in a linear, branched or cyclic configuration or a substituted aromatic compound; and wherein $R_3$ is selected so that the resorcinol derivative inhibits enzymatic browning.

2. A method of claim 1 wherein $R_3$ comprises a heteroatom, a saturated or unsaturated alkyl group, a substituted aromatic group or an organic functional group containing a heteroatom.

3. A method of claim 2 wherein $R_3$ comprises at least one heteroatom which is selected from the group consisting of: oxygen, nitrogen, sulfur, phosphorus, chlorine, bromine, iodine and fluorine.

4. A method of claim 2 wherein $R_3$ is a saturated or unsaturated alkyl group having from about 1 to about 30 carbon atoms in a linear, branched or cyclic configuration.

5. A method of claim 2 wherein $R_3$ is an alkyl group or organic functional group containing a heteroatom selected from the group consisting of: oxygen, nitrogen, sulfur, phosphorus, chlorine, bromine, iodine or fluorine.

6. A method of claim 1 wherein $R_1$ and $R_2$ are both H.

7. A method of inhibiting enzymatic browning of foods or beverages susceptible to such browning, comprising applying to the foods or beverages an amount of a resorcinol derivative sufficient to inhibit browning of the foods, wherein the resorcinol derivative has the following formula:

Formula II

8. A method of claim 7 wherein the foods are selected from the group consisting of: crustaceans, shellfish, fruits, vegetables fruit juices and wines.

9. A method of claim 7 wherein the enzyme is polyphenol oxidase.

10. A method of claim 7 wherein the amount of Formula II sufficient to inhibit browning of the foods is from about 0.0001 to about 0.1% by weight.

11. A method for inhibiting enzymatic browning of foods or beverages susceptible to such browning, comprising applying to the foods or beverages an amount of a resorcinol derivative sufficient to inhibit the browning of the foods, wherein the resorcinol derivative has the following general formula:

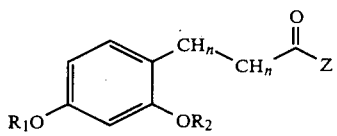 Formula III wherein n is 1 or 2; $R_1$ and $R_2$ are independently selected from the group consisting of: H, $CH_3$, $COR'$, $CR'$, $PO_3R'R''$ and $SO_3R'R''$ wherein $R'$ and $R''$ are independently H, an alkyl group having from about 1 to about 6 carbon atoms in a linear, branched or cyclic configuration or a substituted aromatic compound; and Z is an alkyl or organic functional group selected so that the resorcinol derivative inhibits enzymatic browning.

12. A method of claim 11 wherein Z is selected from the group consisting of: OH, $NH_2$, $O(CH_2)_xCH_3$, $NHCO_2(CH_2)_xCH_3$, $NH(CH_2)_xCH_3$, amino acids, a polyamine substituent selected from the group consisting of: $NH(CH_2)_xNH_2$, $NH(CH_2)_xNH(CH_2)_yNH_2$, $NH(CH_2)_xNHR_4$ and $NH(CH_2)_xNH(CH_2)_yNHR_4$ wherein x and y are independently an integer from 0 to 5; and higher polyamine oligomers or substituted oligomers consisting of at least three 1, diaminoalkane monomers wherein $R_4$ has the following formula:

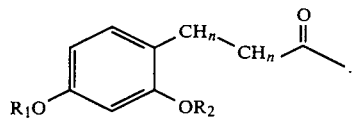

13. A method of claim 11 wherein the resorcinol derivative has the following formula:

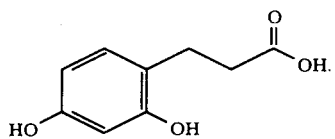 Formula IV

14. A method of claim 11 wherein the resorcinol derivative has the formula:

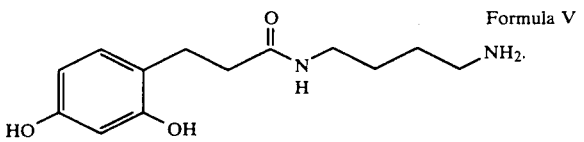 Formula V

15. A method of claim 11 wherein the resorcinol derivative has the following formula:

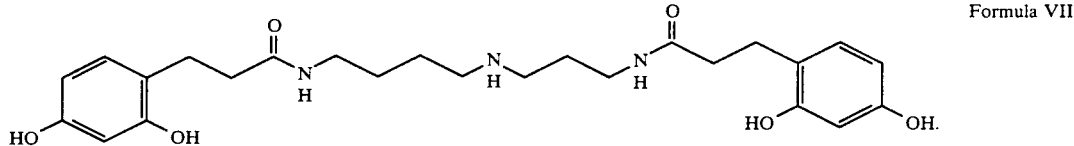 Formula VI

16. A method of claim 11 wherein the resorcinol derivative has the following formula:

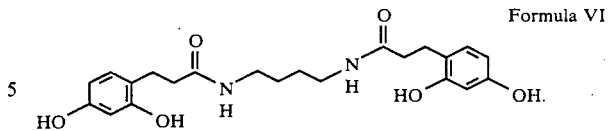 Formula VII

17. A method of inhibiting enzymatic browning of foods or beverage susceptible to such browning, comprising applying to the foods or beverages a resorcinol derivative sufficient to inhibit browning of the foods, wherein the resorcinol derivative has the following formula:

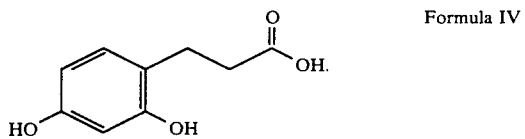 Formula IV

18. A method of claim 17 wherein the foods are selected from the group consisting of: crustaceans, shellfish, fruits, vegetables, fruit juices and wines.

19. A method of claim 17 wherein the enzyme is polyphenol oxidase.

20. A method of claim 17 wherein the amount of Formula IV sufficient to inhibit browning is from about 0.001 to about 0.1 percent by weight.

21. A method of inhibiting enzymatic browning of foods or beverages susceptible to such browning, comprising applying to the foods or beverages a resorcinol derivative sufficient to inhibit browning of the foods wherein the resorcinol derivative has the following formula:

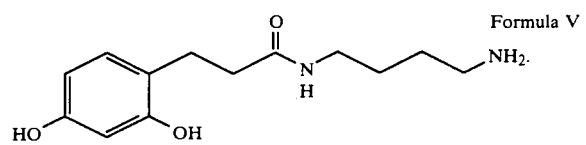 Formula V

22. A method of claim 21 wherein the foods are selected from the group consisting of: crustaceans, shellfish, fruits, vegetables, fruit juices and wines.

23. A method of claim 21 wherein the enzyme is polyphenol oxidase.

24. A method of claim 21 wherein the amount of Formula V sufficient to inhibit browning is from about 0.001 to about 0.1% by weight.

25. A method of inhibiting enzymatic browning of foods or beverages susceptible to such browning, comprising applying to the foods or beverages a resorcinol derivative sufficient to inhibit browning of the foods, wherein the resorcinol derivative has the following formula:

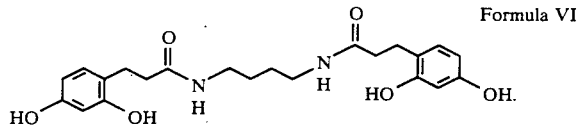

Formula VI

26. A method of claim 25 wherein the foods are selected from the group consisting of: crustaceans, shellfish, fruits, vegetables, fruit juices and wines.

27. A method of claim 25 wherein the enzyme is polyphenol oxidase.

28. A method of claim 25 wherein the amount of Formula VI sufficient to inhibit browning is from about 0.001 to about 0.1% by weight.

29. A method of inhibiting enzymatic browning of foods or beverages susceptible to such browning, comprising applying to the foods or beverages a resorcinol derivative sufficient to inhibit browning of the foods, wherein the resorcinol derivative has the following formula:

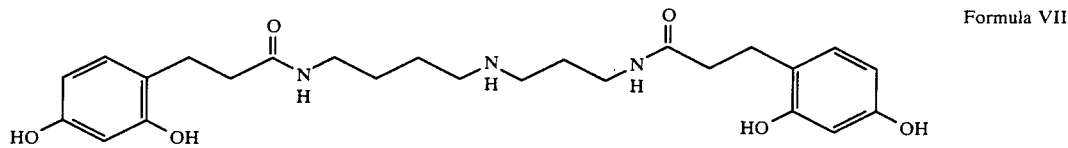

30. A method of claim 29 wherein the foods are selected from the group consisting of: crustaceans, shellfish, fruits, vegetables, fruit juices and wines.

31. A method of claim 29 wherein the enzyme is polyphenol oxidase.

32. A method of claim 29 wherein the amount of Formula VII sufficient to inhibit browning is from about 0.001 to about 0 1% by weight.

33. A composition for inhibiting enzymatic browning of foods or beverages susceptible to such browning, consisting essentially of a resorcinol polyamine derivative having the following formula:

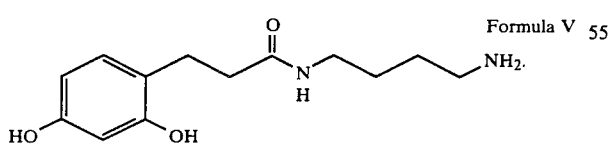

Formula V

34. A composition of claim 33 which is dissolved in an aqueous medium to form an aqueous solution of Formula V.

35. A composition of claim 34 wherein the aqueous solution contains from about 0.001 to about 0.1 percent by weight of Formula V.

36. A composition for inhibiting enzymatic browning of foods or beverages susceptible to such browning, consisting essentially of a resorcinol polyamine derivative having the following formula:

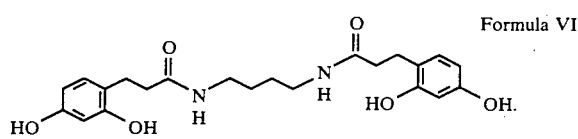

Formula VI

37. A composition of claim 36 which is dissolved in an aqueous medium to form an aqueous solution of Formula VI.

38. A composition of claim 37 wherein the aqueous solution contains from about 0.001 to about 0.1% by weight of Formula VI.

39. A composition for inhibiting enzymatic browning of foods or beverages susceptible to such browning, consisting essentially of a resorcinol polyamine derivative having the following formula:

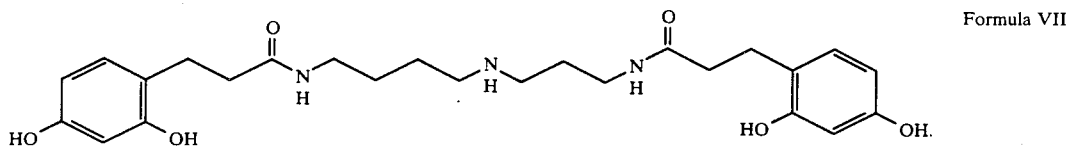

Formula VII

40. A composition of claim 39 which is dissolved in an aqueous medium to form an aqueous solution of Formula VII.

41. A composition of claim 40 wherein the aqueous solution contains from about 0.001 to about 0.1 percent by weight of Formula VII.

42. A food or beverage susceptible to enzymatic browning which has been treated with an amount of resorcinol derivative sufficient to prevent or inhibit browning of the food or beverage wherein the resorcinol derivative is one or more compounds represented by the following general formula:

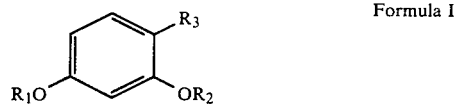

Formula I wherein $R_1$ and $R_2$ are independently selected from the group consisting of: H, $CH_3$, $COR'$, $CR'$, $PO_3R'R''$ and $SO_3R'R''$ wherein $R'$ and $R''$ are independently H or an alkyl group having from 1 to 6 carbon atoms in a linear, branched or cyclic configuration or a substituted aromatic compound; and wherein $R_3$ is selected so that the resorcinol derivative inhibits enzymatic browning.

43. A food or beverage susceptible to enzymatic browning of claim 42 wherein the resorcinol derivative is selected from the group consisting of:

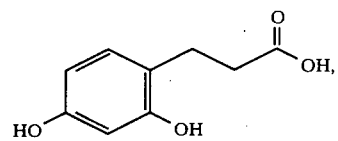
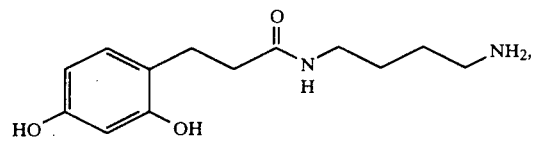
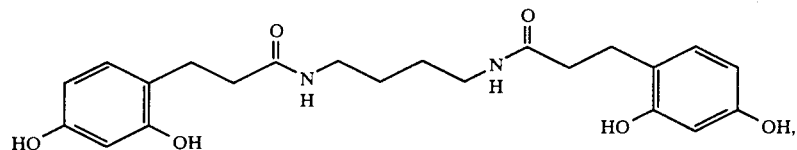
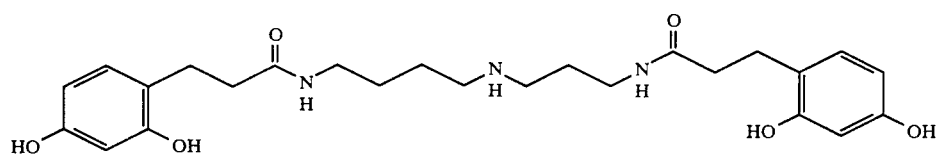
and
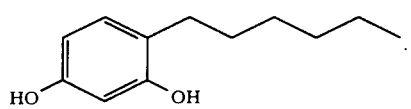
* * * * *